United States Patent
Gabriel et al.

(10) Patent No.: US 6,905,655 B2
(45) Date of Patent: Jun. 14, 2005

(54) MODIFICATION OF SELECTIVITY FOR SENSING FOR NANOSTRUCTURE DEVICE ARRAYS

(75) Inventors: Jean-Christophe P. Gabriel, Pinole, CA (US); Philip G. Collins, Irvine, CA (US); Keith Bradley, Oakland, CA (US); George Gruner, Los Angeles, CA (US)

(73) Assignee: Nanomix, Inc., Emeryville, CA (US)

( * ) Notice: Subject to any disclaimer, the term of this patent is extended or adjusted under 35 U.S.C. 154(b) by 0 days.

(21) Appl. No.: 10/388,701

(22) Filed: Mar. 14, 2003

(65) Prior Publication Data

US 2003/0175161 A1 Sep. 18, 2003

Related U.S. Application Data

(63) Continuation-in-part of application No. 10/099,664, filed on Mar. 15, 2002.
(60) Provisional application No. 60/366,566, filed on Mar. 22, 2002.

(51) Int. Cl.[7] .................. G01N 21/00; G01N 31/22; G01N 15/06; G01N 33/00; G01N 35/00
(52) U.S. Cl. .................. 422/82.01; 422/50; 422/55; 422/56; 422/57; 422/58; 422/68.1; 422/69; 422/82.02; 422/83; 422/90; 422/98; 436/43; 436/63; 436/64; 436/65; 436/66; 436/68; 436/71; 436/73; 436/74; 436/75; 436/149; 436/150; 436/151; 204/193; 204/194; 204/400; 204/403.01; 204/403.03; 204/406; 204/407; 73/1.01; 73/1.02; 73/19.01; 73/23.2; 73/53.01; 438/48; 438/49
(58) Field of Search .................. 422/50, 55, 56, 422/57, 58, 68.1, 69, 88, 82.01, 82.02, 83, 90, 98; 436/43, 63, 64, 65, 66, 68, 71, 73, 74, 75, 149, 150, 151; 204/193, 194, 400, 403.01, 403.03, 403.13, 406, 407; 73/1.01, 1.02, 19.01, 23.2, 53.01; 438/48, 49

(56) References Cited

U.S. PATENT DOCUMENTS

3,676,820 A 7/1972 Taguchi .................. 338/34

(Continued)

FOREIGN PATENT DOCUMENTS

WO    WO 01/44796 A1    11/2000    .......... G01N/27/12

(Continued)

OTHER PUBLICATIONS

Bachtold, A; Hadley, P; Nakanishi, T; Dekker, C; Science 294 (2001) p. 1317.

(Continued)

*Primary Examiner*—Jill Warden
*Assistant Examiner*—Brian Sines
(74) *Attorney, Agent, or Firm*—O'Melveny & Myers LLP

(57) ABSTRACT

An electronic system for selectively detecting and identifying a plurality of chemical species, which comprises an array of nanostructure sensing devices, is disclosed. Within the array, there are at least two different selectivities for sensing among the nanostructure sensing devices. Methods for fabricating the electronic system are also disclosed. The methods involve modifiying nanostructures within the devices to have different selectivity for sensing chemical species. Modification can involve chemical, electrochemical, and self-limiting point defect reactions. Reactants for these reactions can be supplied using a bath method or a chemical jet method. Methods for using the arrays of nanostructure sensing devices to detect and identify a plurality of chemical species are also provided. The methods involve comparing signals from nanostructure sensing devices that have not been exposed to the chemical species of interest with signals from nanostructure sensing devices that have been exposed to the chemical species of interest. Nanostructure sensing device array structures that can measure and subtract out environmental factors are also disclosed.

24 Claims, 23 Drawing Sheets

U.S. PATENT DOCUMENTS

| | | | |
|---|---|---|---|
| 3,831,432 A | | 8/1974 | Cox .............................. 73/23 |
| 4,101,906 A | | 7/1978 | Dahlstrom ................... 346/75 |
| 4,389,658 A | | 6/1983 | Perna ......................... 346/140 |
| 4,542,640 A | | 9/1985 | Clifford ........................ 73/23 |
| 4,759,210 A | | 7/1988 | Wohltjen ....................... 73/23 |
| 5,238,729 A | * | 8/1993 | Debe .......................... 428/142 |
| 5,571,401 A | | 11/1996 | Lewis ......................... 205/787 |
| 5,877,580 A | | 3/1999 | Swierkowski ............... 310/328 |
| 6,289,328 B2 | | 9/2001 | Shaffer ........................ 706/20 |
| 6,312,097 B1 | | 11/2001 | Brugman ..................... 347/40 |
| 6,321,588 B1 | | 11/2001 | Bowers ..................... 73/24.01 |
| 6,528,020 B1 | | 3/2003 | Dai .............................. 422/98 |
| 6,569,490 B2 | * | 5/2003 | Yadav et al. .................. 427/58 |
| 6,673,644 B2 | * | 1/2004 | Gole et al. ..................... 438/49 |
| 2002/0117659 A1 | | 8/2002 | Lieber .......................... 257/14 |

FOREIGN PATENT DOCUMENTS

| | | | | |
|---|---|---|---|---|
| WO | WO 01/03208 A1 | 1/2001 | .......... | H01L/45/00 |
| WO | WO 02/48701 A2 | 6/2002 | .......... | G01N/27/00 |

OTHER PUBLICATIONS

Bahr, J.L., Tour, J., "Highly Functionalized Carbon Nanotubes Using in situ Generated Diazonium Compounds," Chem. Mater. 13 (2001) p. 3823.

Bahr, J.L., Yang, J., Kosynkin, D., Bronikowski, M., Smalley, R., Tour, J., "Functionalization of Carbon Nanotubes by Electrochemical Reduction of Aryl Diazonium Salts: A Bucky Paper Electrode", J. Am. Chem. Soc. 123 (2001) p. 6536.

Collins, P., Arnold, M., Avouris, P., "Engineering Carbon Nanotubes and Nanotube Circuits using Electrical Breakdown," Science 292 (2001) p. 706.

Collins, P., Bradley, K., Ishigami, M., Zettl, A., "Extreme Oxygen Sensitivity of Electronic Properties of Carbon Nanotubes," Science 287 (2000) p. 1801.

Cosandey, F., Skandan, G., Singhal, A., "Materials and Processing Issues in Nanostructured Semiconductor Gas Sensors," JOM–e 52 10 (2000), http://www tms.org/pubs./journals/JOM/0010/Cosandey/Cosandey–0010.html.

Derycke, V; Martel, R; Appenzeller, J; Avouris, P., "Carbon Nanotube Inter– and Intramolecular Logic Gates," Nano Letters 1 No. 9 (2001) p. 453.

Hirsch, A., "Functionalization of Single–Walled Carbon Nanotubes," Angew. Chem. Int. Ed. 41 (2002) p. 1853.

Kong, J., Franklin, N., Zhou, C., Chapline, M., Peng, S., Cho, K., Dai, H., "Nanotube Molecular Wires as Chemical Sensors, " Science 287 (2002) p. 622.

Martel, R; Derycke, V; Lavoie, C; Appenzeller, J; Chan, K.K; Tersoff, J; Avouris, P., Physical Review Letters 87 (2001) p. 256805–1.

Nygard, J; Cobden, D.H.. Applied Physics Letters 79 (2001) p. 4216.

Tans, S; Verschueren, A. Dekker, C; Nature 393 (1998) p. 49.

Zhang, Y; Dai, H; Applied Physics Letters 77 (2000) p. 3015.

Zhang, Y; Franklin, N.W.; Chen R.J.; Dai, H; Chemical Physics Letters 331 (2000) p. 35.

* cited by examiner

MODIFICATION OF SELECTIVITY FOR SENSING FOR NANOSTRUCTURE DEVICE ARRAYS

DOMESTIC PRIORITY CLAIM

This application repeats a substantial portion of prior application Ser. No. 10/099,664, filed Mar. 15, 2002, and adds and claims additional disclosure not presented in the prior application. Since this application names an inventor or inventors named in the prior application, it is a continuation-in-part of the prior application. The priority of U.S. Provisional Application No. 60/366,566, filed Mar. 22, 2002, is also claimed.

BACKGROUND OF THE INVENTION

1. Field of the Invention

This invention relates generally to a system for detecting and identifying chemical species and, more particularly, to a system that uses an array of nanostructure sensing devices, which have been modified for selectivity for sensing a plurality of chemical species and methods of fabricating the same.

2. Description of the Related Art

Chemical and biological sensing is important in many industrial, medical, agricultural, and environmental monitoring applications. Many industrial processes are monitored and kept within control limits by chemical sensing. Medical analyte sensors can determine levels of various chemicals in blood and other body fluids. There is a need to monitor environmental hazards, such as pollutants and biotoxins. Increasingly, there is a demand for chemical sensing with military application, such as detection of harmful chemical and biological agents and for treaty verification. Other applications include sensing simple odors, such as for foodstuffs (e.g., to determine freshness, grade quality, and maturity of cheeses and to identify flavors,), drinks (e.g., to classify wines, beers, whiskies and to analyze flavors as for coffee), perfumes and essential oils.

Some chemical sensors rely on solid state materials, such as semiconducting metal oxides. For example, a metal oxide semiconductor sensor has been described by Taguchi in U.S. Pat. No. 3,676,820. The electrical resistance of the metal oxide semiconductor sensor changes when chemical species are absorbed onto the sensor. These sensors operate best at high temperatures in order to achieve enhanced chemical reactivity between chemical species and sensor materials for significant sensitivity. Solid state sensors have long recovery times, poor reproducibility, and can detect only a limited variety of chemical species. Solid state sensors are limited by their lack of sensitivity to certain chemical species and by their non-linear response.

Other chemical detectors for detecting at the molecular level rely on polymer coated surface acoustic wave (SAW) sensors to detect and identify chemical species. A SAW sensor array has been described by Bowers et al. in U.S. Pat. No. 6,321,588. A SAW sensor operates in effect as a microbalance through the de-tuning of the crystal's resonant frequency as mass is added to its surface. When a SAW sensor is used as part of an oscillator, changes in the characteristics of acoustic waves propagating through the SAW sensor can be used to determine the nature of one or more substances that has adsorbed onto the sensor. The signal transduction mechanism involves somewhat complicated electronics, requiring frequency measurement to 1 Hz while sustaining a 100 MHz Rayleigh wave in the crystal.

There are chemical detectors for detecting gases and vapors that have been developed, which use gas chromatography. This method offers extremely good selectivity in separating chemical compounds. However, the gas chromatographic approach requires a significant amount of time for all chemical species to be detected, as they must be detected serially, which is very time-consuming. Furthermore, systems of this type are not small enough for many field applications.

Accordingly, there is a need for robust, sensitive and accurate sensors capable of detecting a wide variety of chemical species that utilize a simple electronic detection principle, can be used for a wide range of applications, can be manufactured easily and have the flexibility to expand their scope as new detection needs arise.

SUMMARY OF THE INVENTION

In accordance with one embodiment of the present invention, an electronic system for selectively detecting and identifying a plurality of chemical species, which comprises an array of nanostructure sensing devices, is provided. Each nanostructure sensing device comprises at least one nanostructure that has a selectivity for sensing chemical species. Within the array, the selectivity of at least one nanostructure sensing device differs from the selectivity of at least one other nanostructure sensing device. The nanostructure sensing devices can include gate electrodes positioned to influence conductivity in the nanostructures.

In accordance with another embodiment of the invention, a method of fabricating an electronic system, comprising an array of nanostructure sensing devices, for selectively detecting and identifying a predetermined number of chemical species is provided. Each nanostructure sensing device in the array comprises at least one nanostructure and at least two contact electrodes. The at least one nanostructure provides electrical coupling between the contact electrodes. Selectivity for sensing of the nanostructures is modified within at least a portion of the array so that at least one nanostructure sensing device produces a measurably changed signal when exposed to the chemical species. Additional portions of the array undergo other modifications until each of the predetermined number of chemical species produces a measurably changed signal from the array of nanostructure sensing devices. Modification can involve using a reactant. The reactant can be a gas, a chemical solution, or an electrochemical solution. The measurably changed signal can be an electrical signal, an optical signal, a mechanical signal or a thermal signal.

In accordance with one aspect of the invention, a variety of reactants can be supplied to the nanostructure sensing devices in the array by a plurality of chemical jets. The nanostructure sensing devices can be modified for selectivity for sensing through a variety of reactions with a variety of reactants. The variety of reactions and reactants can supply a variety of selectivity for sensing within the array of nanostructure sensing devices such that each of the predetermined number of chemical species produces a measurably changed signal from the array.

In accordance with another aspect of the invention, the reactant is an electrochemical solution, and at least a portion of the array of nanostructure sensing devices is submerged in the reactant. A first voltage is applied to the contact electrodes in at least the portion of the array, and a second voltage, different from the first voltage, is applied to counter electrodes, thus effecting an electrochemical reaction between the electrochemical solution and the nanostructures within at least the portion of the array of nanostructure sensing devices. The electrochemical reaction is repeated, using different electrochemical solutions each time, until there is a variety of selectivity for sensing within the array of nanostructure sensing devices such that each of the predetermined number of chemical species produces a measurably changed signal from the array.

According to another aspect of the invention, nanostructure sensing devices, supplied with reactants, can be modified by applying a characteristic voltage across the contact electrodes. Initially, there is a current flow through the nanostructures. The characteristic voltage continues to be applied until the current flow decreases sharply, thereby introducing point defects into the nanostructures in a self-limiting reaction. The point defects themselves can have selectivity for sensing, or they can serve as attachment sites for further reactions with other molecules, which can have selectivity for sensing.

In accordance with another embodiment of the invention, methods for detecting a plurality of chemical species in a surrounding environment are provided. In one arrangement, first signals are measured from nanostructure sensing devices in an array before exposing the array to a surrounding environment. Second signals are measured from nanostructure sensing devices in the array after exposing the array to the surrounding environment. The signals can be measured while the nanostructures are under the influence of a gate voltage. A series of first and second signals can be made as a function of a series of gate voltages. A significant change between the first signals and the second signals from the array of nanostructure sensing devices indicates detection of a chemical species. Correlations are made between known signal changes that occur when known chemical species are detected and observed changes between the first signals and the second signals.

In another arrangement, an array of sets of nanostructure sensing devices is provided, each set comprising at least two nanostructure sensing devices that have the same selectivity for sensing. Within each set, at least one device is shielded to be impermeable to at least the plurality of chemical species of interest, and at least one device is at least partially exposed to at least the plurality of chemical species. Signals from the devices in each set are measured and compared after positioning the array in the environment of interest. Correlations are made between known signal differences for shielded and at least partially exposed nanostructure sensing devices when known chemical species are detected and observed differences in signals for shielded nanostructure sensing devices and at least partially exposed nanostructure sensing devices in the array of sets. Again, gate voltages or a series of gate voltages can be employed while making the measurements. The signals can be electrical signals, optical signals, mechanical signals, or thermal signals.

Further features and advantages of the present invention will become apparent to those of ordinary skill in the art in view of the detailed description of embodiments below, when considered together with the attached drawings and claims.

DETAILED DESCRIPTION OF THE EMBODIMENTS

Recently, nanostructures have attracted attention as sensor components. Coating of nanotubes to make nanostructure sensing devices has been described by Zhang et al. in Chemical Physics Letters 331 (2000), p. 35 and by Zhang et al. in Applied Physics Letters 77 (2000), p. 3015. Nanostructure sensing devices show great promise for many applications. They can be made very small; even an array with a large number of nanostructure sensing devices can be made very small. They can be modified to detect a wide variety of chemical species. They use very little power. But in general, nanostructure sensing devices have been made only in small quantities for lab testing, and the techniques for producing nanostructure sensing devices have not been developed for large-scale manufacturing.

The embodiments of the present invention are illustrated in the context of using an array of nanostructure sensing devices to detect a plurality of chemical or biological species. The skilled artisan will readily appreciate, however, that the materials and methods disclosed herein will have application in a number of contexts where sensing of multiple chemical or biological species is desired.

These and other objects and advantages of the present invention will become more fully apparent from the following description taken in conjunction with the accompanying figures. Reference will now be made to the figures wherein like numerals refer to like parts throughout.

Figure 1:
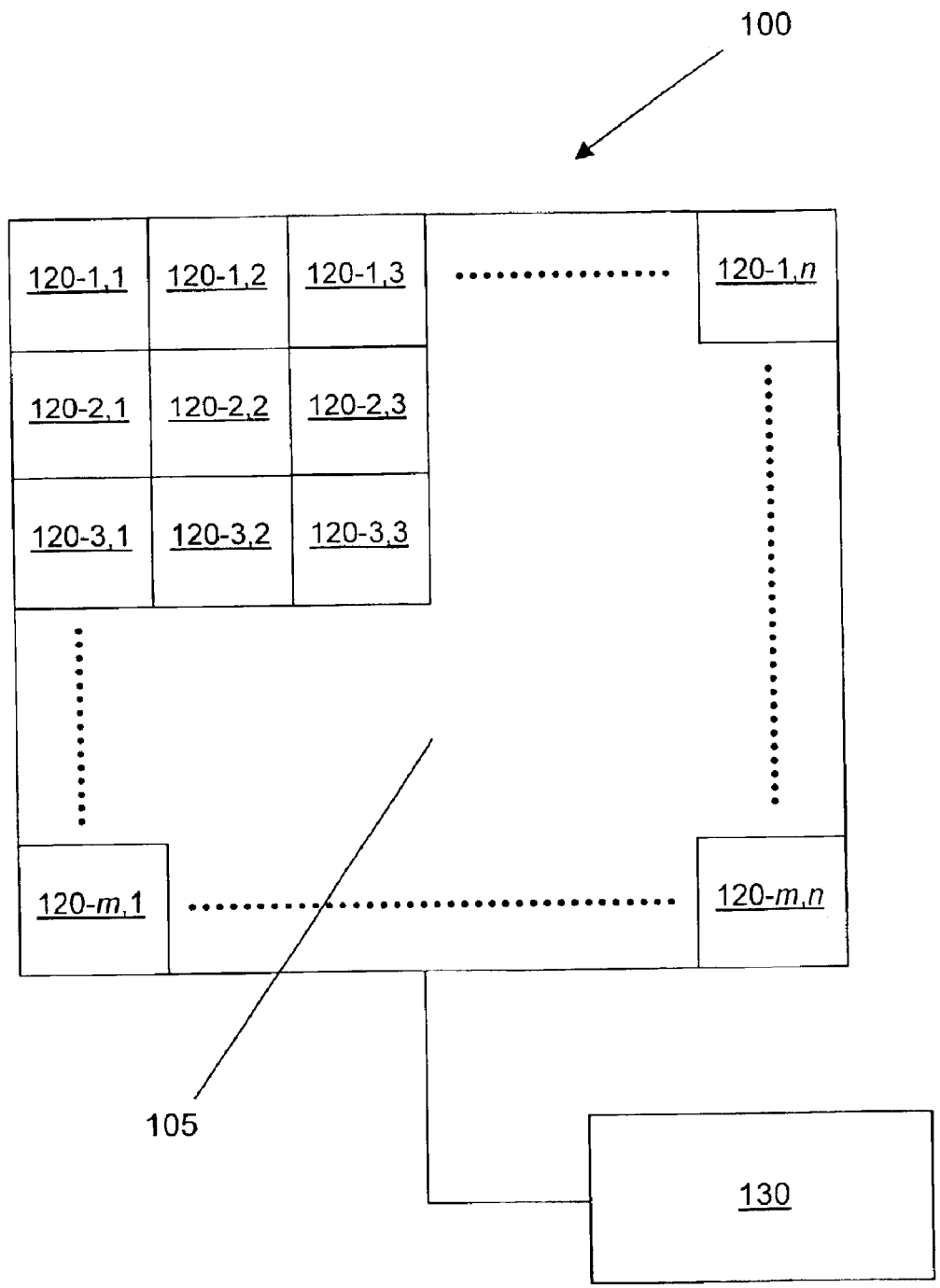
FIG. 1 is a schematic drawing of an electronic system for selectively detecting and identifying a plurality of chemical or biological species.

FIG. 1 is a schematic illustration of an electronic system 100 for selectively detecting and identifying a plurality of chemical or biological species. The system 100 includes an array 105 of nanostructure sensing devices 120-$a,b$, wherein, for the purpose of this illustration, a designates the row number, and b designates the column number of each device up to a maximum of m rows and n columns, where a, b, m, n are all integers. Each nanostructure sensing device 120-$a,b$ has at least one nanostructure, and the at least one nanostructure in each device 120-$a,b$ has a particular selectivity for sensing chemical or biological species. The species can be detected in either liquid or gaseous environments.

Selectivity for sensing is used here to mean that the nanostructure responds selectively to a chemical or biological species in a way that produces a measurably changed and reproducible signal from the nanostructure sensing device. A measurably changed signal means that a signal produced by the nanostructure sensing device before exposure to the species of interest is measurably different from a signal produced by the same nanostructure sensing device after exposure to the species of interest. Signals can include electrical, optical, mechanical and thermal signals. The selectivity for sensing for each nanostructure sensing device is different from at least one other nanostructure sensing device in the array.

In other arrangements, there can be a wide variety of selectivity for sensing among the nanostructure sensing devices 120-$a,b$ in the array 105, so that a large number of species can be detected. Total selectivity, that is, complete selectivity of a species by a single nanostructure sensing device, may or may not be obtained, but the responses of individual nanostructure sensing devices are reproducible, and their resulting signals are well-characterized. These signals can be analyzed to identify the species detected. Any species can be identified as long as it generates a unique and differential response across a plurality of sensors in the array.

The measurably changed signals of the nanostructure sensing devices indicate the presence of chemical or biological species. Measurable signals can include electrical signals, optical signals, mechanical signals and thermal signals. The set of changes in signal from the nanostructure sensing devices provides a basis for interpretation and analysis to identify species which are present. The sets of signals from the array 105 before exposure and after exposure to species of interest can be relayed to a processing system 130, where interpretation and analysis can be performed to provide species identification.

Nanostructure sensing devices are highly sensitive; they are known to respond to a number of environmental factors as well as a target species for which they have selectivity for sensing and for which sensing is desired. Therefore, a signal produced by a nanostructure sensing device can be the result of many factors. In the case of chemical or biological sensing in gases, a nanostructure sensing device responds to at least non-chemical environmental factors and humidity, as well as to the target species. In the case of chemical or biological sensing in liquids, a nanostructure sensing device responds to at least non-chemical and non-biological environmental factors and pH, as well as to the target species, in the solutions of interest.

Figure 2:
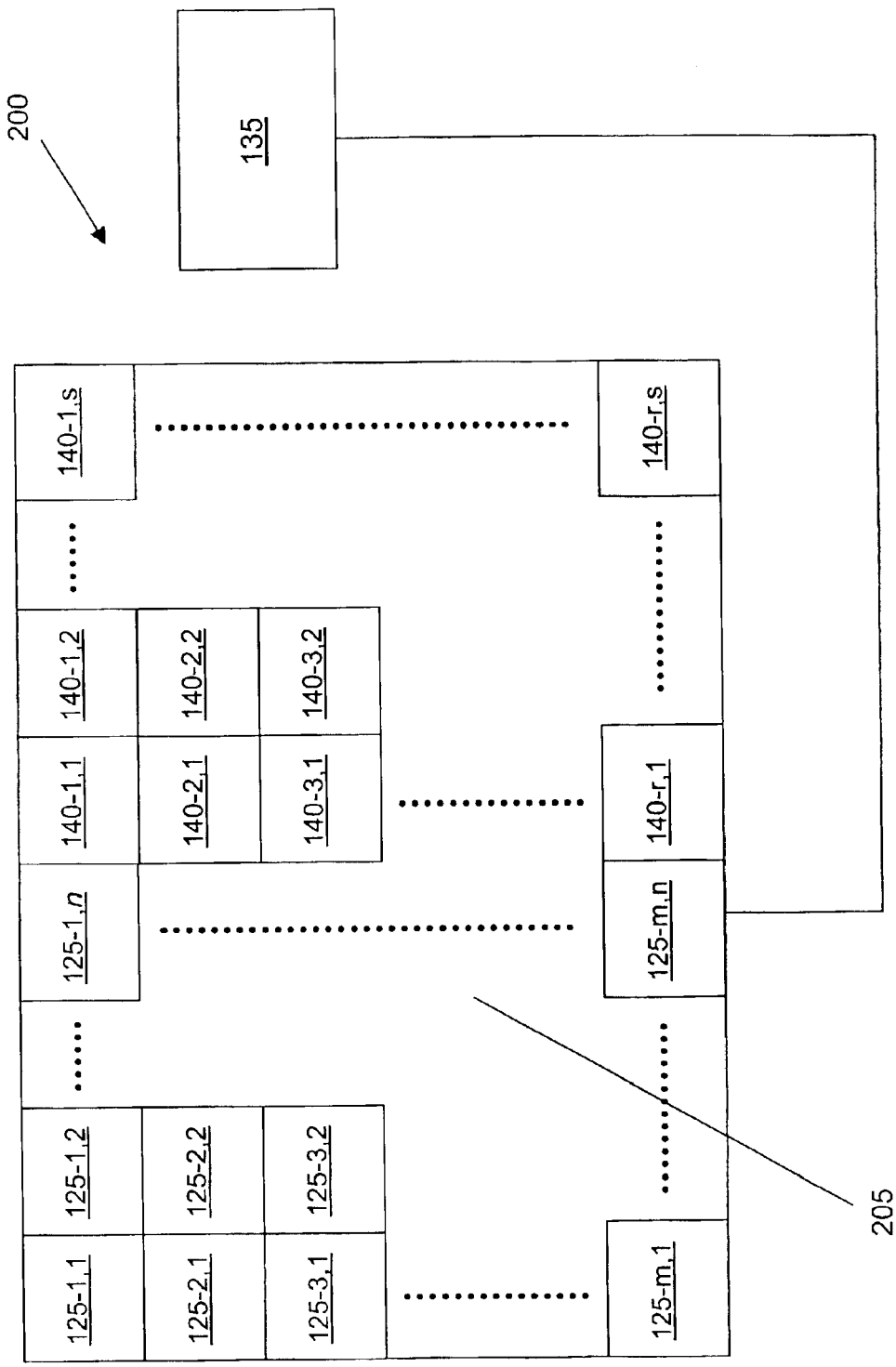
FIG. 2 is a schematic drawing of an electronic system for measuring environmental factors and selectively detecting and identifying a plurality of chemical or biological species.

In addition to nanostructure devices with selectivity for sensing for target chemical or biological species, it can be useful to include within a nanostructure sensing device array, devices that are adapted to respond to environmental factors with little or no response to chemical or biological species. FIG. 2 is a schematic illustration of an electronic system 200 for selectively detecting and identifying a plurality of chemical or biological species and environmental factors. The system 200 includes an array 205 of devices, which includes both nanostructure sensing devices 125-$a,b$, wherein each device has a particular selectivity for sensing chemical or biological species and nanostructure sensing device, wherein each device has sensitivity to at least one environmental factor. The nanostructure sensing devices 140-$a,b$ can also have sensitivity to sensing for at least some target species, as will be discussed in more detail below. As for the devices in FIG. 1, a designates the row number, and b designates the column number of each device up to a maximum of m rows and n columns for chemical and biological sensors and a maximum of r rows and s columns for environmental sensors, where a, b, m, n, r, s are all integers. Each nanostructure sensing device 125-$a,b$, 140-$a,b$ has at least one nanostructure. The devices can be respond in either liquid or gaseous environments. Sets of signals from the array 205 before exposure and after exposure to species of interest can be relayed to a processing system 135, where interpretation and analysis can be performed to provide species identification and information about environmental factors. Within the processing system 135, the environmental factors can also be used to deconvolute environmental components from nanostructure sensing device signals to aid in species identification.

Figure 3:
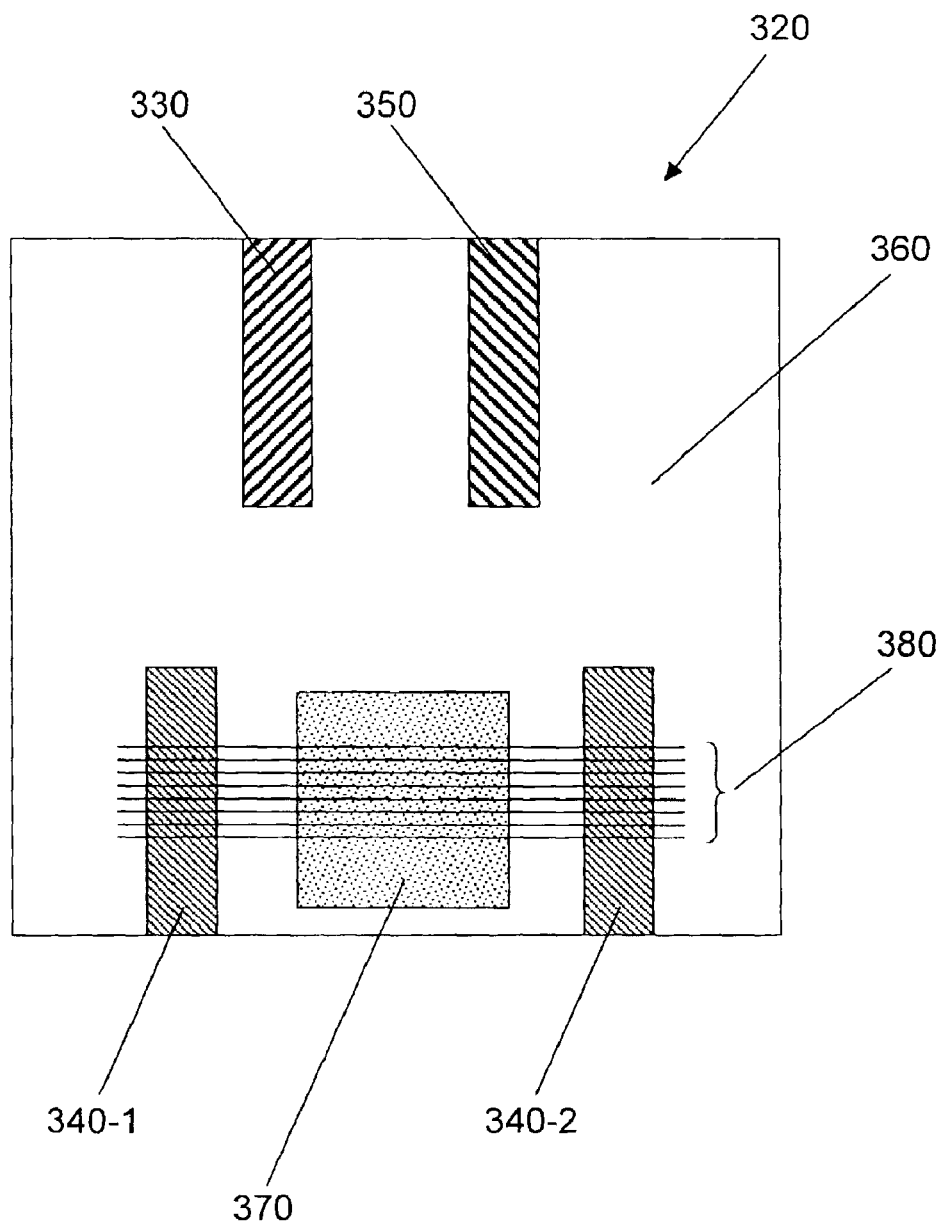
FIG. 3 shows an individual nanostructure sensing device according to an embodiment of the invention.

FIG. 3 is a schematic illustration of a single nanostructure sensing device 320 according to an embodiment of the invention. The nanostructure sensing device 320 has two contact electrodes 340-1, 340-2 lying over a substrate 360, but any number n of contact electrodes 340-$a$ can be used.

The substrate 360 can be a semiconductor material and can be overlaid by an insulating layer as is known in the art of semiconductor manufacturing. The electrodes 340-1, 340-2 are conducting elements made of any conducting material consistent with semiconductor manufacturing. Examples include aluminum, copper, titanium and tungsten. A group of nanostructures 380 are in electrical contact with the contact electrodes 340-1, 340-2, or the n contact electrodes 340-*n*, and extend along the space between the contact electrodes. The group of nanostructures 380 can contain one or more individual nanostructures. In some arrangements, most or all of the nanostructures 380 make contact with the contact electrodes 340-1, 340-2. In other arrangements, only a small portion of the nanostructures 380 make contact with either one or all contact electrodes 340-1, 340-2, or with the n contact electrodes 340-*n*. In some arrangements, the nanostructures 380 are pre-formed and positioned on the substrate either before or after formation of the contact electrodes 340-1, 340-2. In other arrangements, the nanostructures 380 are grown in place over the substrate 360 and make contact with the contact electrodes 340-1, 340-2. In some arrangements, the nanostructures 380 are in contact with the substrate 360 between the contact electrodes 340-1, 340-2. In other arrangements, the nanostructures 380 are suspended above the substrate 360 with an intervening space between the nanostructures 380 and the substrate 360. In some arrangements (not shown), there is a protective coating on the contact electrodes 340-1, 340-2. In some arrangements, the protective coating covers also portions of the nanostructures 380, especially the portions of the nanostructures 380 where the nanostructures 380 make contact with the contact electrodes 340-1, 340-2. Materials that can be used for the protective coating include silicon oxides, metal oxides, polymer films, and nonvolatile organics.

For the purposes of this disclosure, nanostructures include forms such as single-walled nanotubes, multi-walled nanotubes, nanofibers, nanowires, nanocoils, nanospheres, nanocages, nanococoons, nanohorns, nanoropes, nanotori, nanorods, nanoplatelets, and other large, extended macromolecules such as polymers, dendrimers, organometallics, and fullerene-like molecules. Nanostructures can include one or several forms. Nanostructures can be turbostratic, highly oriented, twisted, straight, curled and rigid. Nanostructures can have zig-zag chirality, or a mixture of chiralities. Nanostructures can be twisted, straight, bent, kinked, curled, flattened, or round. Nanostructures having an approximately linear form can be arranged in bundles of structures, such as ropes, braids or twisted bundles. Nanostructures can be empty, filled, and multifaceted. Nanostructures can be made of any element known to form nanostructures, for example, carbon, boron, carbon nitride, boron nitride, or carbon boron nitride. The chemical composition of a nanostructure can be homogeneous or can vary throughout the structure. Nanostructures can have cracks, dislocations, branches or other imperfections.

Nanostructures, as used in the embodiments disclosed herein, can have approximately linear forms, i.e., forms that can extend to make contact with one or more electrodes. An approximately linear form can be achieved by using nanostructures that have an approximately linear form naturally, such as nanotubes, nanofibers, nanowires, nanoropes and nanorods. Alternatively, nanostructures having other forms, such as nanospheres, nanocages, nanococoons and nanotori, can be combined with one another or with other nanostructures to create an overall approximately linear form. Within an array of nanostructure sensing devices, the nanostructures can vary from nanostructure sensing device to nanostructure sensing device.

In FIG. 3 and according to another aspect of the invention, the nanostructure sensing device 320 can include a counter electrode 330. The nanostructure sensing device 320 can also include a pseudo-reference electrode 350. In other arrangements, there can be more than one counter electrode and more than one pseudo-reference electrode. The counter electrode 330 and pseudo-reference electrode 350 can be used in an electrochemical reaction to modify selectivity for sensing of the group of nanostructures 380, as will be explained later. Materials commonly used for counter electrodes 330 and pseudo-reference electrodes 350 include graphite and metals.

In other arrangements, and also shown in FIG. 3, the nanostructure sensing device 320 can include a gate electrode 370 positioned to influence conductivity in the nanostructures 380. Although the gate electrode 370 is shown as a discreet region in the substrate 360 in FIG. 3, the gate electrode can take many forms, including an undifferentiated gate electrode, as are known in the semiconductor arts.

Figure 4:
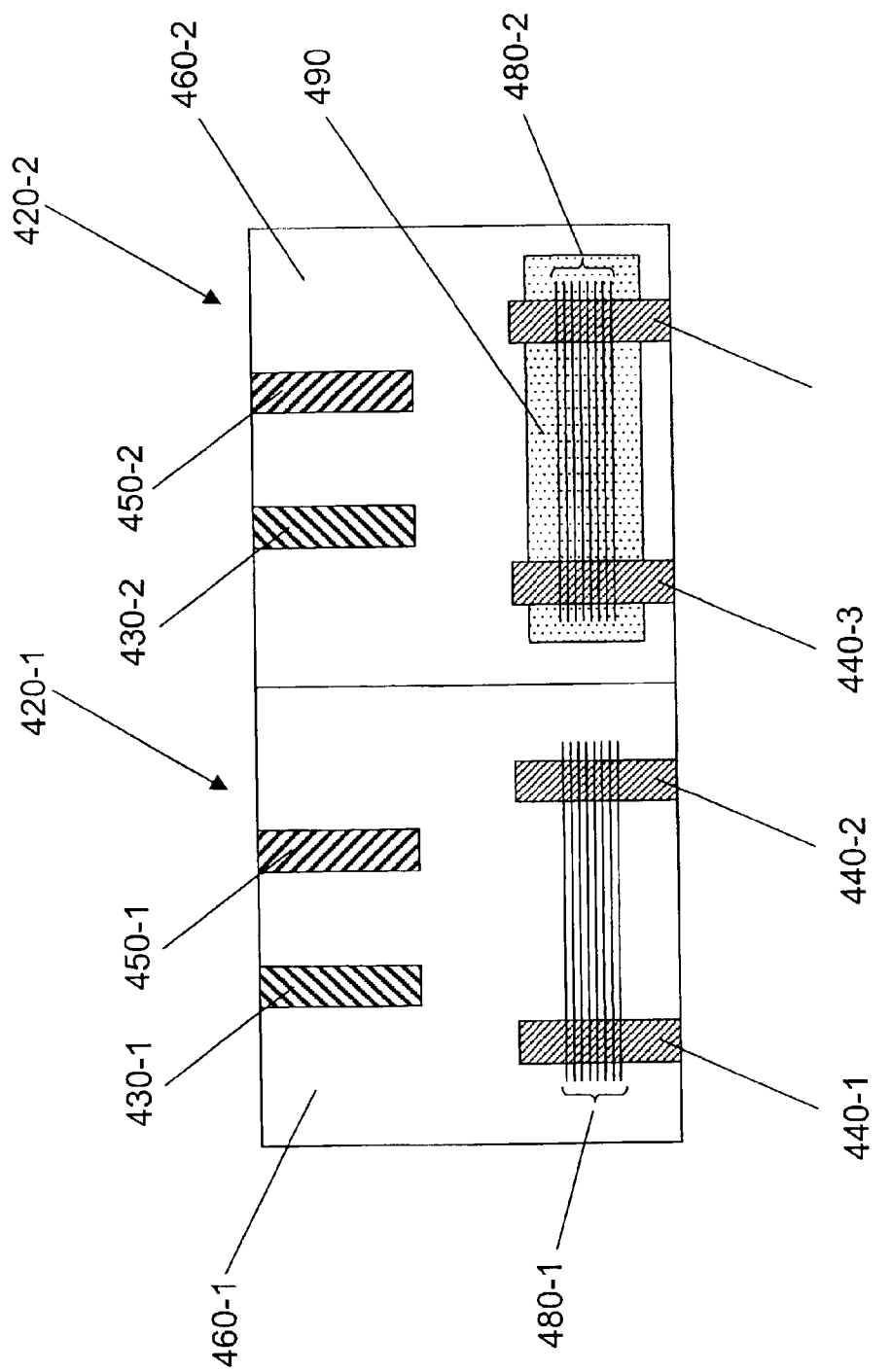
FIG. 4 shows a pair of nanostructure sensing devices having the same selectivity for sensing chemical species. The nanostructures in one of the nanostructure sensing devices are at least partially shielded from the environment, and the nanostructures in the other nanostructure sensing device are at least partially exposed to the environment, according to an embodiment of the invention.

FIG. 4 shows schematically a set of nanostructure sensing devices 420-1, 420-2. The nanostructure sensing device 420-1 has a pair of contact electrodes 340-1, 340-2, a substrate 460-1, a group of nanostructures 480-1 having an approximately linear form, a counter electrode 430-1 and a pseudo-reference electrode 450-1 as have been discussed above in reference to FIG. 3. The nanostructure sensing device 420-2 has a pair of contact electrodes 340-3, 340-4, a substrate 460-2, a group of nanostructures 480-2 having an approximately linear form, a counter electrode 430-2 and a pseudo-reference electrode 450-2 as have been discussed above in reference to FIG. 3. The groups of nanostructures 480-1, 480-2 have been modified to have the same selectivity for sensing The nanostructures 480-1 in nanostructure sensing device 420-1 can be fully exposed to a surrounding environment, as shown in FIG. 3. In other arrangements, the nanostructures 480-1 can be partially shielded by permeable or selectively permeable membranes so that nanostructures 480-1 are at least partially exposed to the species of interest in the surrounding environment. As shown in FIG. 4, the nanostructures 480-2 in nanostructure sensing device 420-2 are covered by a shield 490 that can be completely impermeable to the surrounding environment. In other arrangements, the shield 490 can be impermeable to at least the species of interest, but still provide less exposure to the surrounding environment than any partial shield on nanostructures 480-2.

The arrangement shown in FIG. 4 can be extended to a whole array of nanostructure sensing devices as has been discussed above in reference to FIG. 2. Within the array, there can be a plurality of sets of nanostructure sensing devices wherein the devices within any one set all have the same selectivity for sensing. In addition, within any one set, the nanostructures in some nanostructure sensing devices can be shielded from at least the species of interest, and the nanostructures in other nanostructure sensing devices can be at least partially exposed to the species of interest in the surrounding environment, as has been described above for the two nanostructure sensing devices 420-1, 420-2 in FIG. 4. The selectivity for sensing for devices in one set can be different from the selectivity for sensing for devices in another set.

Figure 5:
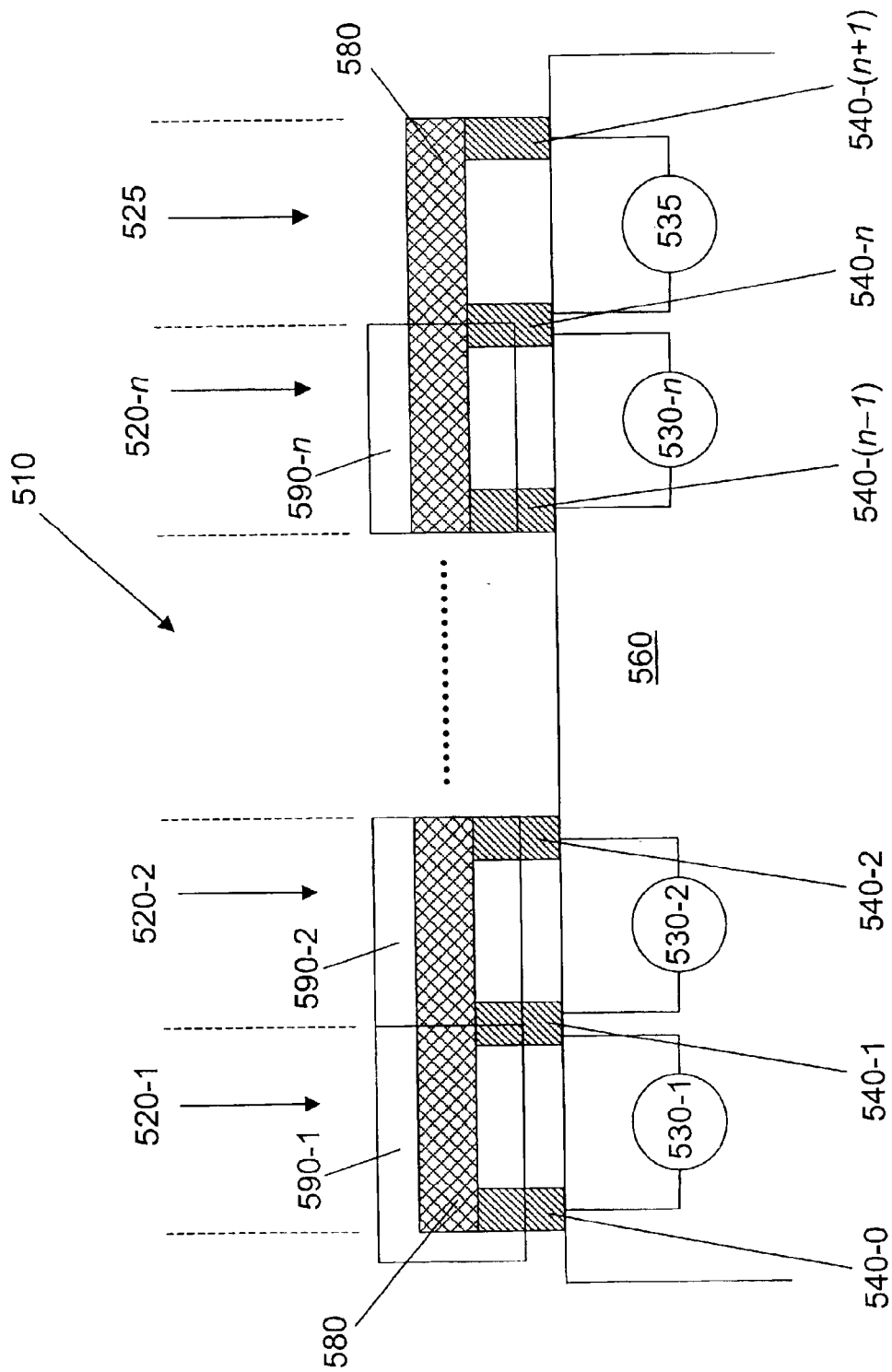
FIG. 5 is a cross-section view of a multi-component nanostructure sensing device, according to an embodiment of the invention.

FIG. 5 is a cross-section view of an (n+1)-component nanostructure sensing device 510 according to an embodiment of the invention. The multi-component nanostructure sensing device 510 includes n+1 nanostructure sensing device components, 520-*a*, 525 and contact electrodes 540-0, 540-1, 540-2, . . . , 540-(n+1) over a substrate 560. Any number of contact electrodes can be used to provide each nanostructure sensing device component 520-1, 520-2, ..., 520-n, 525 with at least two electrical connections separated by lengths of one or more intervening nanostructures 580. The substrate 560 can be a semiconductor material and can be overlaid by an insulating layer as is known in the art of semiconductor manufacturing. The electrodes 540-0–540-(n+1) are conducting elements made of any conducting material consistent with semiconductor manufacturing. Examples include aluminum, copper, titanium and tungsten. In this example, one nanostructure 580 is shown in electrical contact with the contact electrodes 540-0–540-(n+1) and extends along the spaces between adjacent contact electrodes 540-a, 540-(a+1). In other arrangements, there can be any number of nanostructures 580 extending along the contact electrodes 540-0–540-(n+1). In yet other arrangements, there can be a network of nanostructures 18 extending along the contact electrodes 540-0–540-(n+1). In the case of a network of nanostructures, some nanostructures within the network may have a length and an orientation that allows them to make contact with all the contact electrodes 540-0–540-(n+1). Other nanostructures may have a length and an orientation that does not allow them to make contact with all the contact electrodes 540-0–540-(n+1), but they may make contact with one or more electrodes 540-0–540-(n+1) and with other nanostructures in the network. . In some arrangements, a sensing component 520-a can include more than two contact electrodes. In some arrangements, the nanostructures 580 are pre-formed and positioned on the substrate 560 either before or after formation of the contact electrodes 540-0–540-(n+1). In other arrangements, the nanostructures 580 are grown in place over the substrate 560 in a way that brings the nanostructures 580 into contact with the contact electrodes 540-0–540-(n+1). In some arrangements, the nanostructures 580 are in contact with the substrate 560 in regions between the contact electrodes 540-0–540-(n+1). In other arrangements, the nanostructures 580 are suspended above the substrate 560 with an intervening space between the nanostructures 580 and the substrate 560.

Nanostructures 580 has selectivity for sensing for a target chemical or biological species. As discussed above, in some arrangements, selectivity for sensing can be achieved by direct chemical or electrochemical modification of the nanostructures 580. In other arrangements, selectivity for sensing can be achieved by depositing a continuous or a discontinuous coating along the length of the nanostructures 580. There are coatings 590-1–590-n on each sensing component 520-1–520-n, respectively. The coatings 590-1–590-n may or may not be in direct contact with the enclosed nanostructures 580, i.e., there may or may not be an intervening enclosed space between the coatings 590-1–590-n and the nanostructures 580. The coatings 590-1–590-n are chosen to isolate the sensing components 520-1–520-n, respectively, from exposure to various components of the surrounding environment, and thus to provide signals 530-1–530-n, each of which can contain information that is independent of one or more environmental factors. Signals 530-1–530-n from the sensing components 520-1–520-n can be used to help deconvolute the signal 535 from nanostructure sensing device 525 to determine whether target species have been detected.

For sensing in a gaseous atmosphere, a response or a signal output 535 of the nanostructure sensing device component 525 is affected at least by chemical or biological species for which the nanostructure sensing device component 525 has selectivity for sensing, but the response can also be affected by non-chemical and non-biological environmental factors such as humidity and temperature. Independent information about environmental factors can be used to help deconvolute the signal output 535 of the nanostructure sensing device 525 to determine whether target species have been detected. Similarly for sensing in liquids, the response or the signal output 535 of a nanostructure sensing device component 525 is affected at least by chemical species for which the nanostructure sensing device component 525 has selectivity for sensing, but the response can also be affected by environmental factors such as temperature and pH of the liquid. Independent information about environmental factors can be used to help deconvolute the signal output 535 of the nanostructure sensing device 525 to determine whether target species have been detected.

Figure 6:
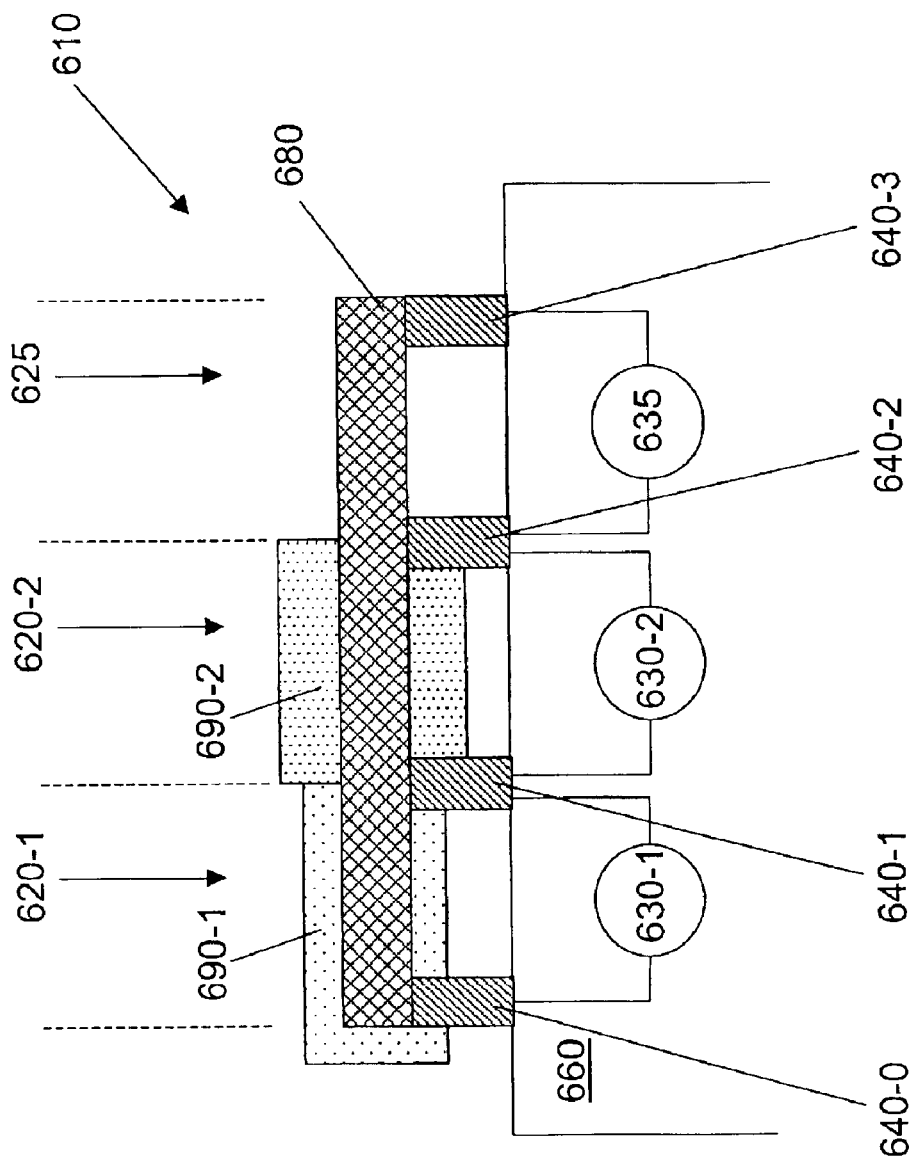
FIG. 6 is cross-section view of a three-component nanostructure sensing device that has components for sensing environmental factors, humidity, and target chemical or biological species, according to embodiments of the invention.

FIG. 6 is a cross-section view of a nanostructure sensing device according to an embodiment of the invention, which shows an example of a multi-component nanostructure sensing device 610 that includes three components 620-1, 620-2, 625 and is designed for chemical or biological sensing in a gaseous environment. Nanostructure 680 has selectivity for sensing for a target species. As discussed above, in some arrangements, selectivity for sensing can be achieved by direct chemical or electrochemical modification of the nanostructure 680. In other arrangements, selectivity for sensing can be achieved by depositing a continuous or a discontinuous coating along the length of the nanostructure 680 or nanostructure component. In nanostructure sensing device component 620-1, the nanostructure 680 is surrounded by an impermeable coating 690-1 and produces a signal 630-1 in response to non-chemical and non-biological environmental factors, such as temperature and electric and magnetic fields. Chemical and biological species are not transmitted through the impermeable coating 690-1. Suitable coatings include dielectric materials such as silicon oxide. It should be understood that, in general, many impermeable coatings cannot block completely transmission of all species.

In nanostructure sensing device component 620-2, the nanostructure 680 is surrounded by a semi-permeable coating 690-2 that can transmit some chemical and biological species, but can block transmission of other species. It should be understood that neither the transmission nor the blocking is total. There are transmission factors for semi-permeable coatings that are properties of the kind of coating and the thickness of the coating and are different for different chemical species. Nanostructure sensing device component 620-2 produces a signal 630-2 in response to environmental factors and at least some transmitted species.

The coatings 690-1, 690-2 are shown with different thicknesses in FIG. 6, but the thicknesses may or may not be the same. The thicknesses are chosen to produce the desired result. It is useful if the coating 690-1 is thick enough to be impermeable to chemical and biological species, including water, but not so thick as to slow down significantly the process of heat conduction from the surrounding environment to the nanostructure 680. It is useful if the coating 690-2 is thick enough to reduce greatly transmission of all species except water, but not so thick as to slow down significantly the transmission of water molecules through the coating 690-2 to the nanostructure 680. Nanostructure sensing device component 625 includes a nanostructure that has selectivity for sensing a target chemical or biological species. The device component 625 can respond also to environmental factors and to other species, such as water, as well as the target species. The device component 625 produces a signal 635 in response some or all of these factors. Thus three signals 630-1, 630-2, 635 are produced by the multi-component nanostructure sensing device 610. Component 620-1 yields a signal 630-1 in response to environmental factors, component 620-2 yields a signal 630-2 in response to environmental factors and water, and component 625 yields a signal 635 is in response to at least environmental factors, humidity, and target species. Any appropriate algorithm can be used to process the three signals and determine whether a target species has been detected.

Figure 7:
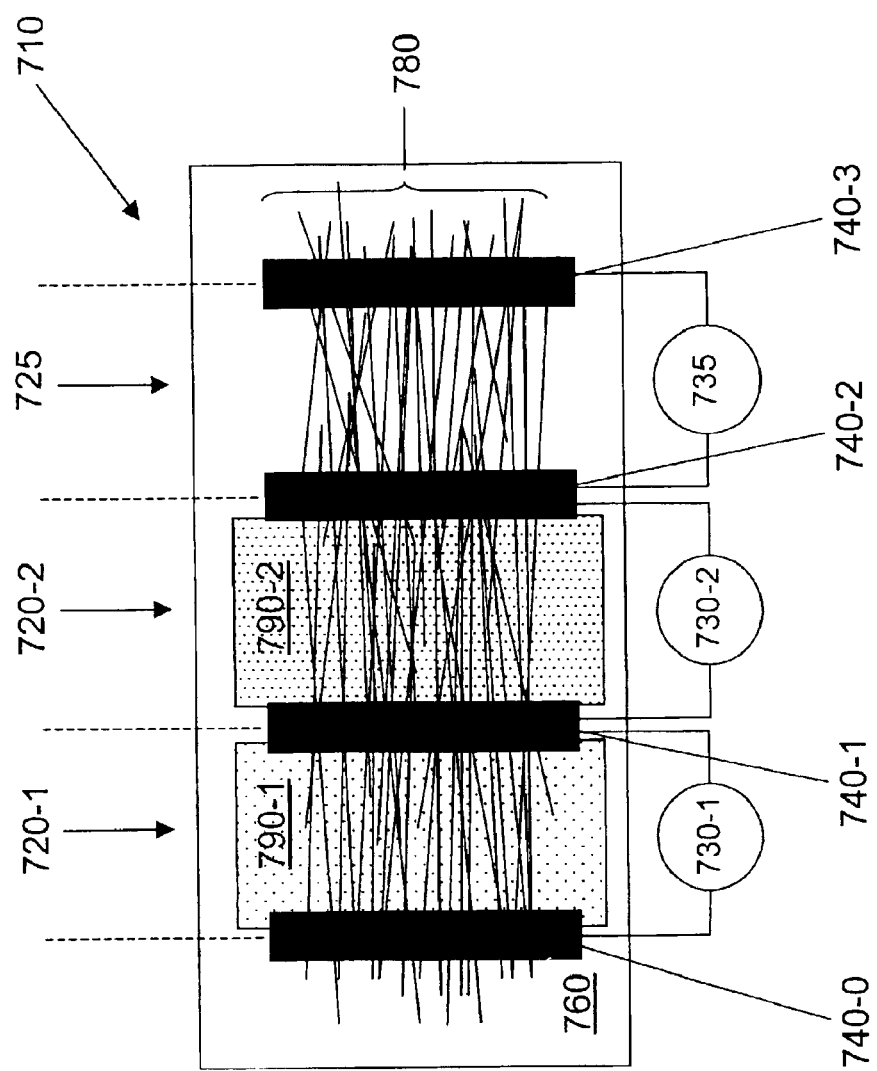
FIG. 7 is top view of a nanostructure sensing device that uses a network of nanostructures and has components for sensing environmental factors, humidity, and target chemical species, according to embodiments of the invention.

FIG. 7 is a top view of a multi-component nanostructure sensing device 710 similar to the one shown in cross section in FIG. 6, which is shown as an example of a nanostructure sensing device 710 case where a network of nanostructures 780 is used as the sensing element.

In another embodiment, nanostructure sensing device components are not segments of a multi-component nanostructure sensing device, as has been discussed above. Each nanostructure sensing device component is a stand-alone nanostructure sensing device that contains its own nanostructure or network of nanostructures, as will be shown below in FIGS. 8, 9, 10. These stand-alone devices can also be put together to form arrays.

Figure 8:
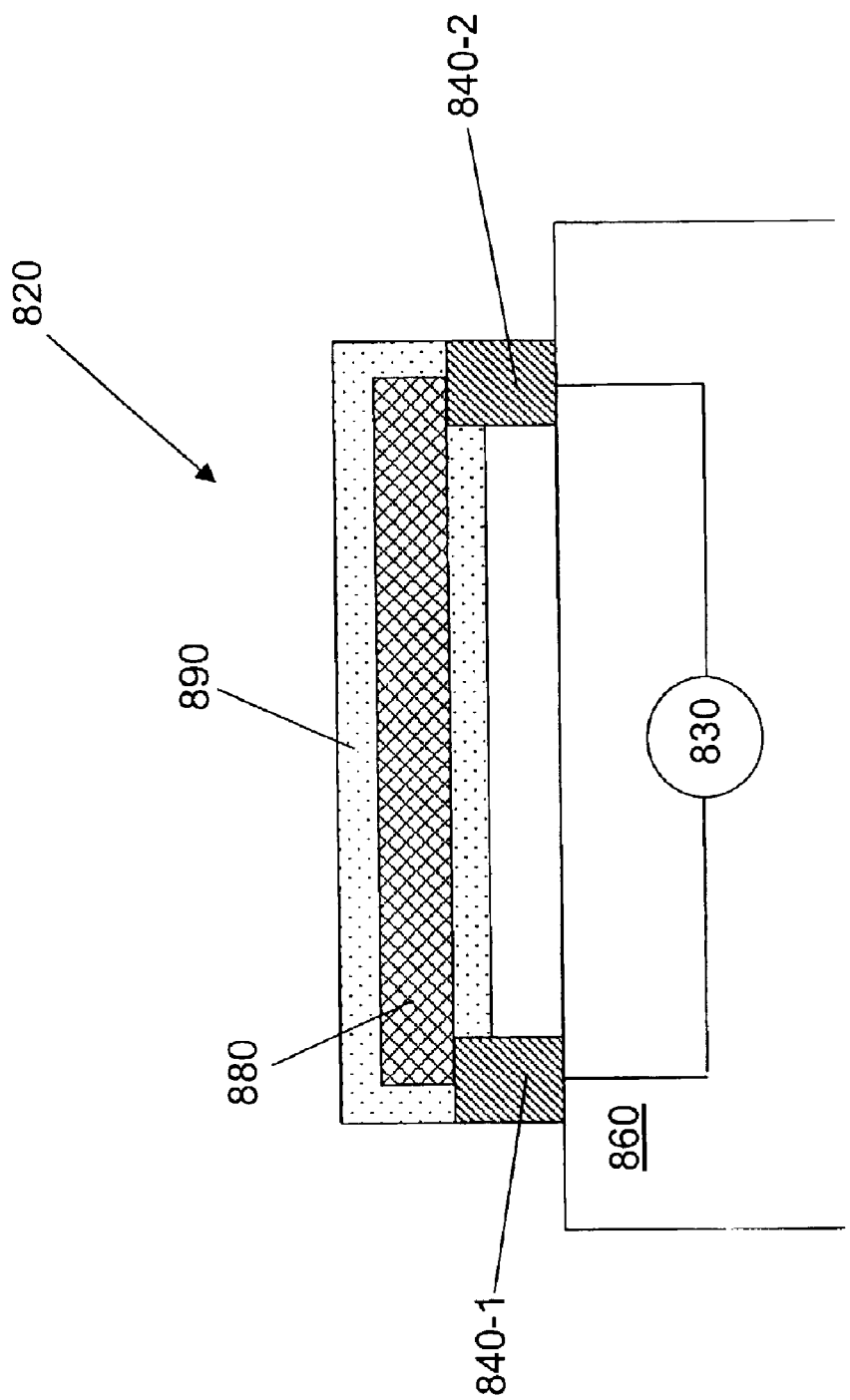
FIG. 8 is a schematic cross-section view of a nanostructure sensing device adapted to sense environmental factors only.

FIG. 8 shows a schematic cross-section view of a nanostructure sensing device 820 that includes a nanostructure or network of nanostructures 880 in electrical contact with two electrodes 840-1, 840-1, all over a substrate 860. A signal 830 is produced by the nanostructure sensing device 820. In the example shown in FIG. 8, the signal is electrical, i.e., the signal is an electrical resistance, an electrical current, or an electrical voltage. In other arrangements and as discussed above, the signal can be optical, mechanical or thermal. The nanostructure or network of nanostructures 880 is covered by an essentially impermeable coating 890. No significant amount of chemical or biological species, including water, can reach the nanostructure or network of nanostructures 880 through the impermeable coating 890. The nanostructure sensing device 820 senses only non-chemical and non-biological environmental factors, such as temperature and electric and magnetic fields, and the output signal 830 is in response basically only to environmental factors.

Figure 9:
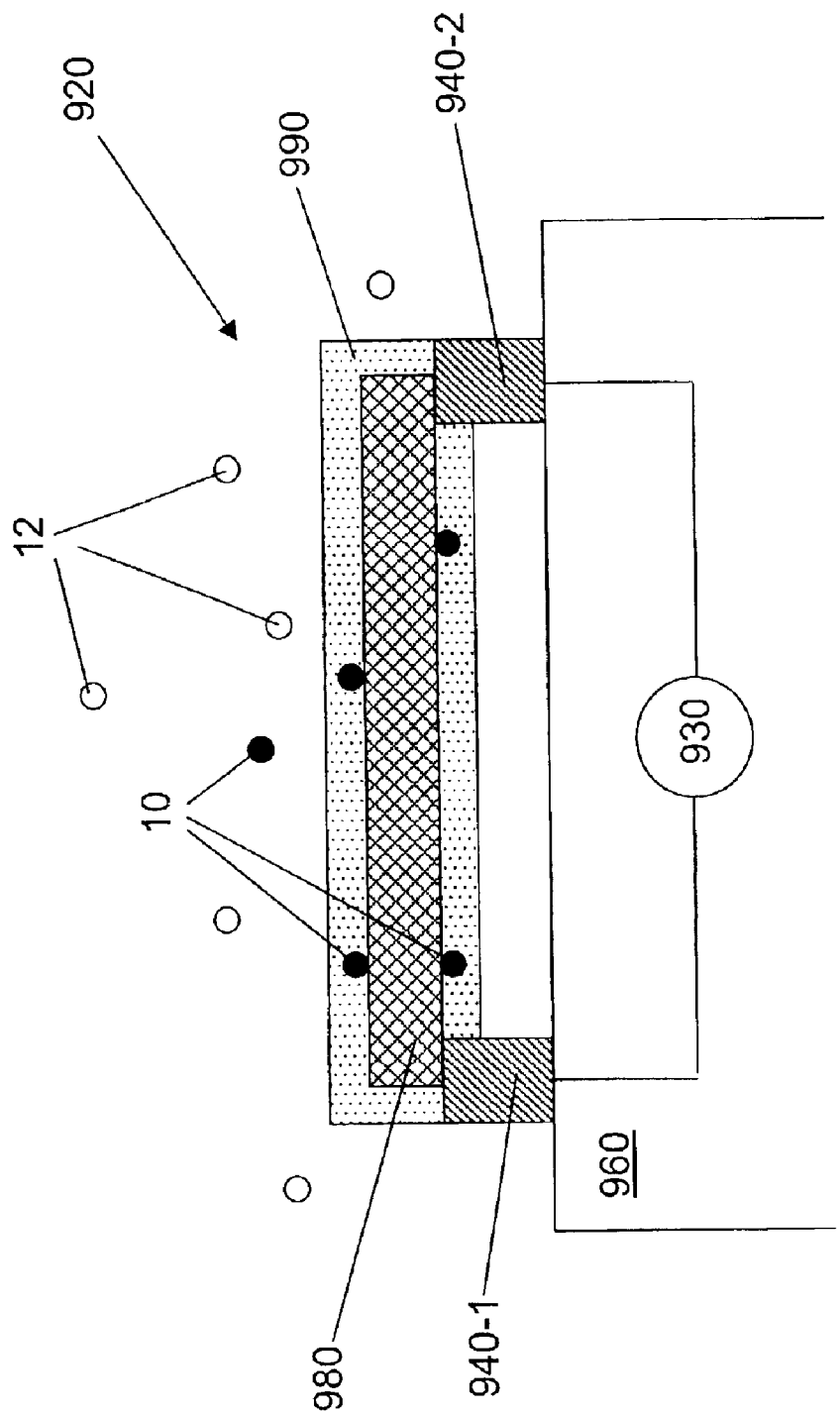
FIG. 9 is a schematic cross section view of a nanostructure sensing device adapted to sense environmental factors and at least humidity, but not a target chemical or biological species.

FIG. 9 shows a schematic cross-section view of a nanostructure sensing device 920 that includes a nanostructure or network of nanostructures 980 in electrical connection with two electrodes 940-1, 940-2, all over a substrate 960. A signal 930 is produced by the nanostructure sensing device 920. In the example shown in FIG. 9, the signal is electrical, i.e., the signal is an electrical resistance, an electrical current, or an electrical voltage. In other arrangements and as discussed above, the signal can be optical, mechanical or thermal. The nanostructure or network of nanostructures 980 is covered by a selectively permeable coating 990. The coating 990 can be a molecular sieve with a high efficiency for transmission of some molecules and a low efficiency for transmission of other molecules to the nanostructure or network of nanostructures 980. In the example shown in FIG. 9, the coating 990 is a molecular sieve with a pore size that transmits water molecules 10 and blocks at least the target chemical or biological species 12. Examples of materials appropriate for coating 990 include small pore-size alumino silicate zeolites that are rich in aluminum. The nanostructure sensing device 920 produces an output signal 930 in response to non-chemical and non-biological environmental factors and to humidity but has very little or no influence from the target species. The output signal 930 reflects the nanostructure sensing device 920 response to humidity and non-chemical and non-biological environmental factors, such as temperature and electric and magnetic fields.

Figure 10:
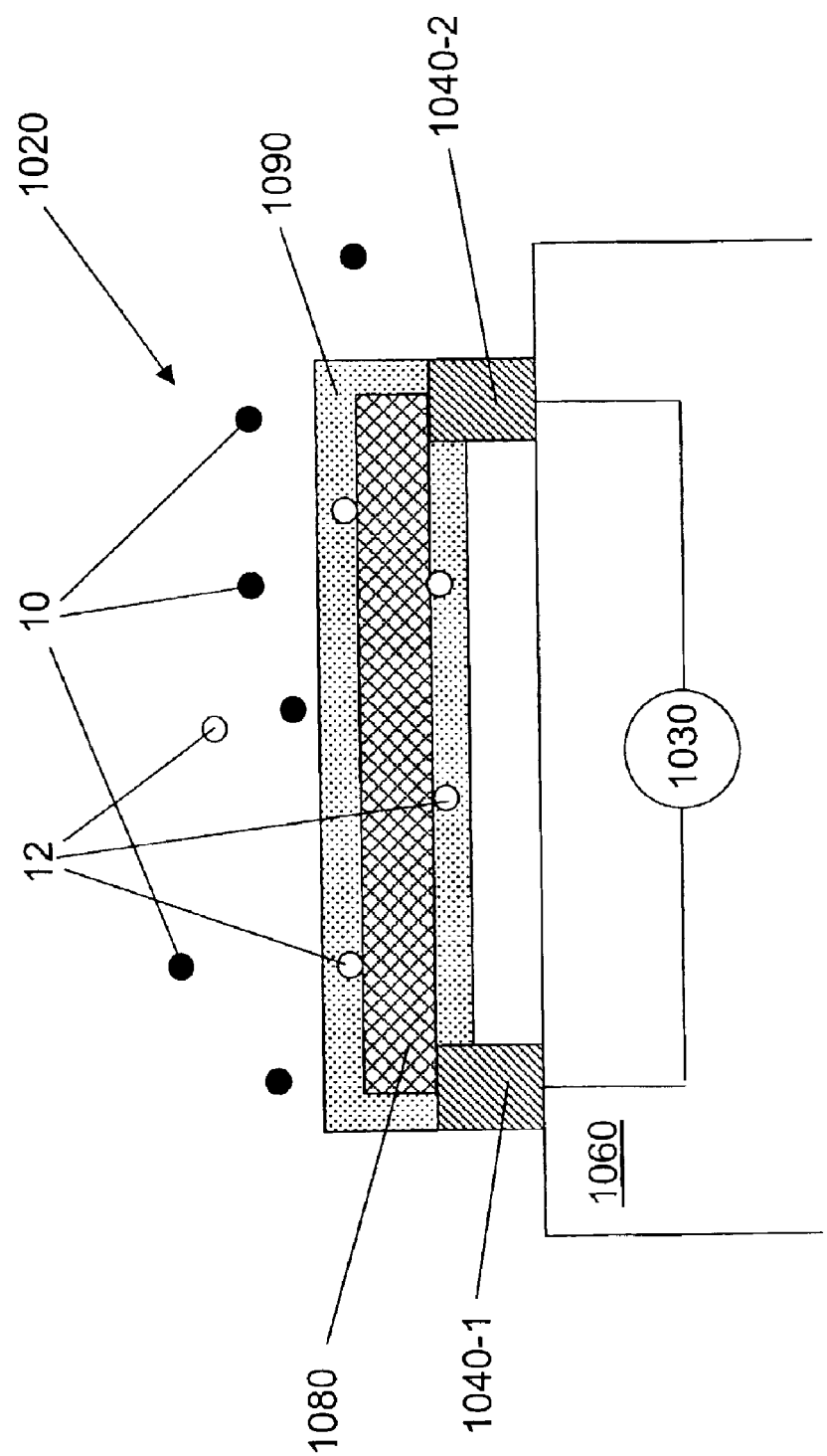
FIG. 10 is a schematic cross section view of a nanostructure sensing device adapted to sense environmental factors and at least a target chemical or biological species, but not humidity.

In an alternative arrangement, FIG. 10 shows a schematic cross-section view of a nanostructure sensing device 1020 that includes a nanostructure or network of nanostructures 1080 in electrical connection with two electrodes 1041-1, 1040-2, all over a substrate 1060. A signal 1030 is produced by the nanostructure sensing device 1020. In the example shown in FIG. 10, the signal is electrical, i.e., the signal is an electrical resistance, an electrical current, or an electrical voltage. In other arrangements and as discussed above, the signal can be optical, mechanical or thermal. The nanostructure or network of nanostructures 1080 is covered by a selectively permeable coating 1090. In this example, the coating 1090 is a microporous hydrophobic membrane that has a low efficiency for transmission of water molecules 10 but has a high efficiency for transmission of at least the target chemical or biological species 12 to the nanostructure or network of nanostructures 1080. Examples of materials appropriate for coating 1090 include pure siliceous zeolites and fluoropolymers. The nanostructure sensing device 1020 can respond to non-chemical and non-biological environmental factors and at least the transmitted target species 12, but has very little or no exposure to water 10 and produces an output signal 1030 accordingly. The output signal reflects the nanostructure sensing device 1020 response to the target species, non-chemical and non-biological environmental factors, such as temperature, electric and magnetic fields, but not humidity.

The selectively permeable coatings 990, 1090 in FIGS. 9 and 10, respectively, have been described in ideal terms. It should be understood that neither the transmission nor the blocking is total. There are transmission factors for semi-permeable coatings, which are properties of the kind and thickness of the coating and are different for different chemical species. In addition, impermeable coatings, such as 890 in FIG. 8 are seldom totally impermeable.

Figure 11:
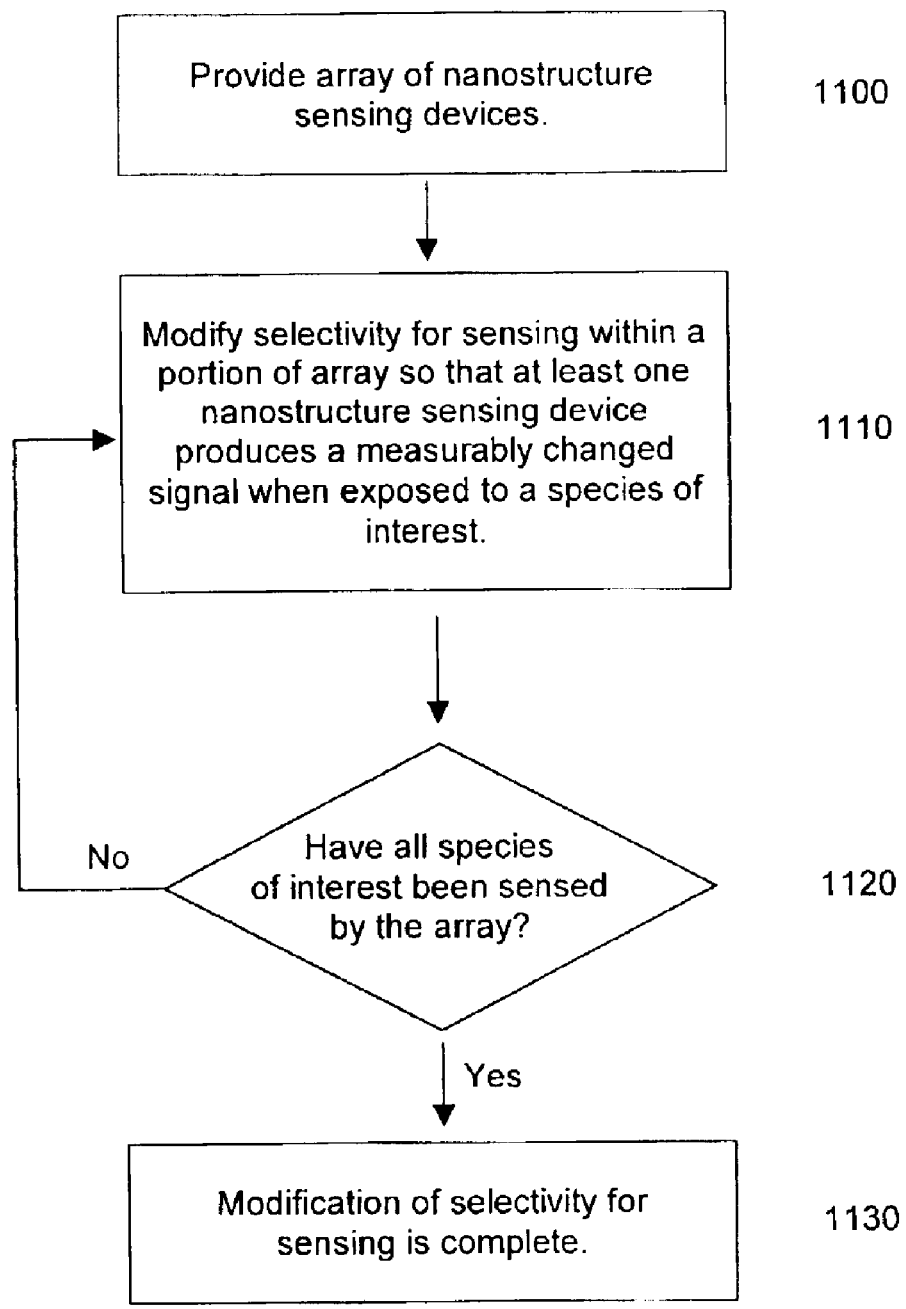
FIG. 11 is a flow chart showing a method of fabricating an electronic system for selectively detecting and identifying a predetermined number of chemical or biological species according to an embodiment of the invention.

FIG. 11 shows a flow chart that summarizes the steps of a method of fabricating an electronic system for selectively detecting and identifying a predetermined number of chemical or biological species of interest. Step 1100 involves providing an array of nanostructure sensing devices. Each nanostructure sensing device includes at least one nanostructure that is connected electrically to at least two contact electrodes. In Step 1110, selectivity for sensing within a portion of the array of nanostructure sensing devices is modified so that at least one nanostructure sensing device produces a measurably changed signal when exposed to the species of interest. A measurably changed signal means that a signal produced by the nanostructure sensing device before exposure to the chemical or biological species of interest is measurably different from a signal produced by the same nanostructure sensing device after exposure to the species of interest. Signals can include electrical, optical, mechanical and thermal signals. Modifying can involve using a reactant, either a liquid or a gas. The reactant can be a chemical solution or an electrochemical solution. Additional energy for the modification can be supplied by ultraviolet, thermal, or electrical energy. In some arrangements, before Step 1110, the contact electrodes can be coated with a material that is impervious to the reactant. In some arrangements, before Step 1110, portions of the nanostructures can be coated with a material that is impervious to the reactant. For example, materials such as silicon oxides, metal oxides, polymer films, and nonvolatile organics can be used for the coatings. Step 1120 involves deciding whether all of the predetermined number of species, i.e., the species of interest, have been sensed by the array. If not all species have been sensed, Step 1110 is performed on another portion of the array so that at least one nanostructure sensing device produces a measurable signal when exposed to at least one of the species that had been found not to be sensed previously in Step 1120. The decision of Step 1120 is made again. As long as there are chemical or biological species of interest that are not sensed by the array, Step 1110 and decision Step 1120 continue to be performed. When the decision at Step 1120 is that all species of interest are sensed by the array of nanostructure sensing devices, the method moves on to Step 1130, wherein modification of selectivity for sensing is complete.

Nanostructures are modified to change the way they respond to species of interest. There are a number of ways in which the modification can be effected. In one example, a material can be deposited (such as by chemical or electrochemical means) onto a nanostructure in a continuous coating. The continuous coating can be highly absorbent for or reactive with a chemical species of interest, but, in any case, the coating interacts strongly with the chemical species of interest, and thus produces a response, such as an electrical, thermal or optical signal. The underlying nanostructure can act essentially as a substrate for the coating.

In another example, the deposited coating is not continuous, but the coating still responds strongly to a chemical species of interest. The response can be communicated to the nanostructure through a variety of means, such as charge transfer, electric dipoles, thermally, or by mechanical strain. The nanostructure can act as a transducer for the response signal.

In yet another example, a deposited coating is not an element of the modification of the nanostructure. A reactant and a nanostructure engage in a reaction, such as a chemical or an electrochemical reaction, which results in a point defect in the nanostructure. As used herein, a point defect is defined to be a site on the nanostructure where the normal arrangement, that is, the arrangement before modification, of chemical bonds is disrupted. This can be a single broken bond, or it can be a small number of missing or rearranged atoms. The point defect can be defined further by its functionality. The point defect is an atomic site or cluster of atomic sites where the chemical nature and reactivity are different from the bulk of the nanostructure. Point defects can have selectivity for sensing. Point defects can also serve as attachment sites for further reactions as will be discussed below with reference to FIG. 16B. Molecules in the reactant and atoms within the nanostructure whose bonds have been disrupted can bond to form other kinds of point defects. The nanostructure can act as both detector of the chemical species and transducer of the response signal.

Chemical jet technology, similar to inkjet technology, allows deposition of droplets of reactants of very small size at precise locations on a given surface. A chemical jet dispenser has been described by Swierkowski (U.S. Pat. No. 5,877,580), which is incorporated by reference herein. A set of reactant reservoirs containing different reactants and delivery channels can be used to deposit a large number of different reactants. Reactant droplet size can be adjusted so that the droplet covers only one nanostructure sensing device or so that one droplet extends over several devices.

Figure 12:
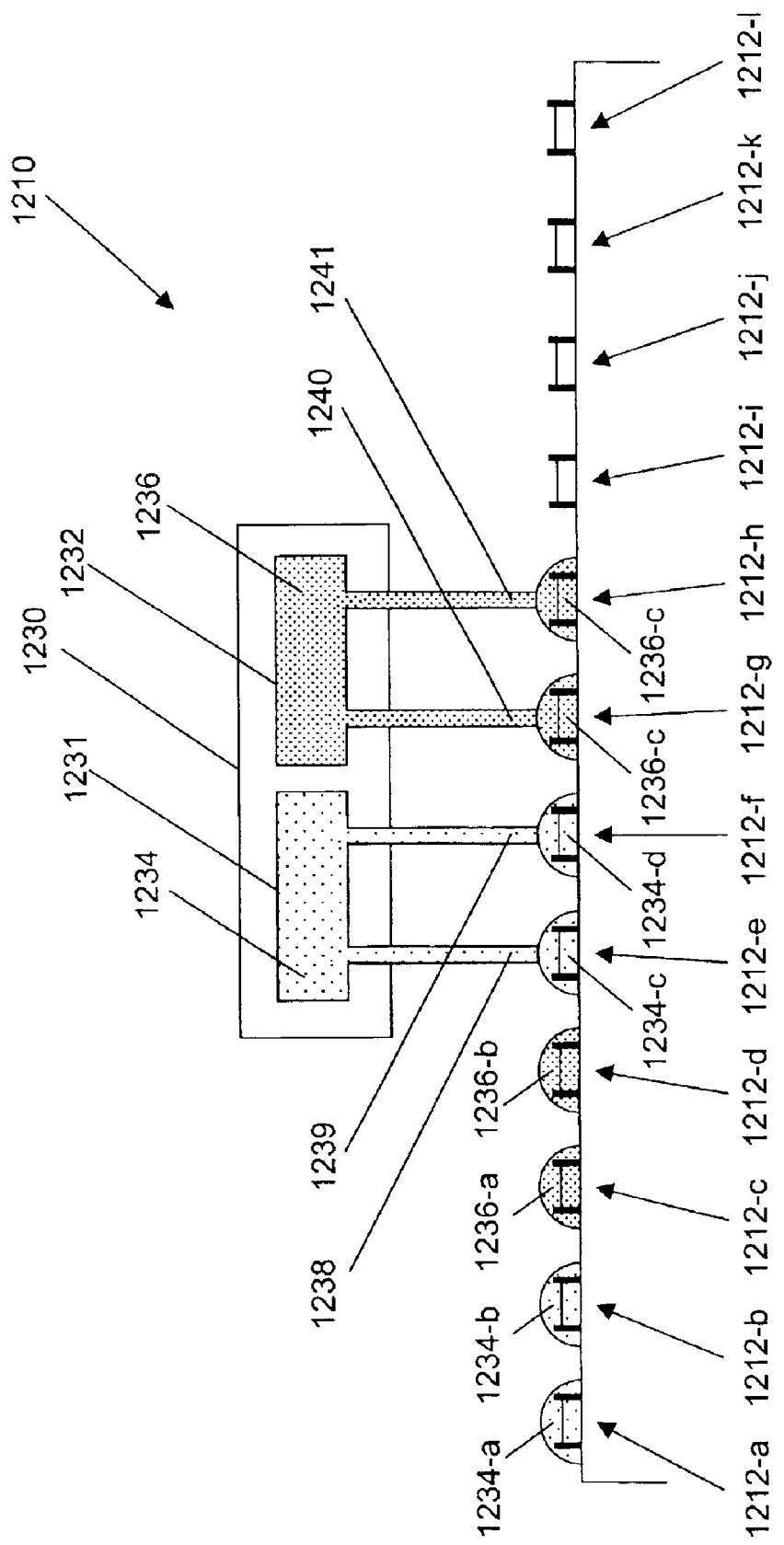
FIG. 12 is a cross-sectional view of chemical jets dispensing drops of reactant onto a portion of an array of nanostructure sensing devices.

FIG. 12 shows schematically a cross-sectional view of a chemical jet system 1230 that dispenses drops of reactant onto nanostructure sensing devices 1212-*a*–1212-*l* on a portion 1210 of an array, according to an illustrated embodiment of the invention. FIG. 12 includes two reactant reservoirs 1231, 1232, each containing a reactant 1234, 1236, respectively. Reactants 1234, 1236 can be the same, or they can be different. Reactant 1234 is dispensed through chemical jets 1238, 1239 and reactant 1236 is dispensed through chemical jets 1240, 1241. In FIG. 12, the chemical jet system 1230 has already dispensed reactant drops 1234-*a*, 1234-*b*, 1236-*a*, 1236-*b* onto nanostructure sensing devices 1212-*a*, 1212-*b*, 1212-*c*, 1212-*d*, respectively. Each nanostructure sensing device receives the reactants that will interact with the nanostructures to achieve the desired modification. The chemical jet system 1230 makes it possible to avoid cross-contamination or cross-reactivity between the individual nanostructure sensing devices 1212-*a*–1212-*l*.

The chemical jet system 1230 of FIG. 12 is positioned over the next set of four nanostructure sensing devices 1212-*e*, 1212-*f*, 1212-*g*, 1212-*h* in the array portion 10. Reactant 1234 leaves reservoir 1231 through chemical jets 1238, 1239 to dispense drops 1234-*c*, 1234-*d* onto nanostructure sensing devices 1212-*e*, 1212-*f*, respectively. Similarly, reactant 1236 leaves reservoir 1232 through chemical jets 1240, 1241 to dispense drops 1236-*c*, 1236-*d* onto nanostructure sensing devices 1212-*g*, 1212-*h*, respectively. In FIG. 12, the chemical jets 1238–1241 are shown in contact with the reactant drops 1234-*c*, 1234-*d*, 1236-*c*, 1236-*d*. In some arrangements, the chemical jets 1238–1241 can include counter electrodes (not shown) and pseudo-reference electrodes (not shown), which can be used to effect electrochemical reactions within the reactant drops 1234-*c*, 1234-*d*, 1236-*c*, 1236-*d*, as will be discussed in more detail with reference to FIG. 13A below.

After the drops 1234-*c*, 1234-*d*, 1236-*c*, 1236-*d* have been dispensed, and after electrochemical reactions that require contact between counter electrodes (not shown) and pseudo-reference electrodes (not shown) in the chemical jets 1238–1241 have occurred, the chemical jet system 1230 moves forward to align the chemical jets 1238–1241 with the next four nanostructure sensing devices 1212-*i*, 1212-*j*, 1212-*k*, 1212-*l* and proceeds with dispensing reactants 1234, 1236.

Although for purposes of illustration, FIG. 12 shows two reactant reservoirs 1231, 1232, four chemical jets 1238–1241, and only a portion 1210 of a nanostructure sensing device array, the skilled artisan will understand readily that this system can include any number of reactant reservoirs and any number of chemical jets to be applied to any size nanostructure sensing device array. A wide variety of stepping patterns across the array can also be employed. Although FIG. 12 shows one drop of reactant for each nanostructure sensing device, it should be understood that in some arrangements, one reactant drop can cover a number of nanostructure sensing devices to modify the selectivity for sensing of the number of nanostructure sensing device in the same way.

Figure 13A:
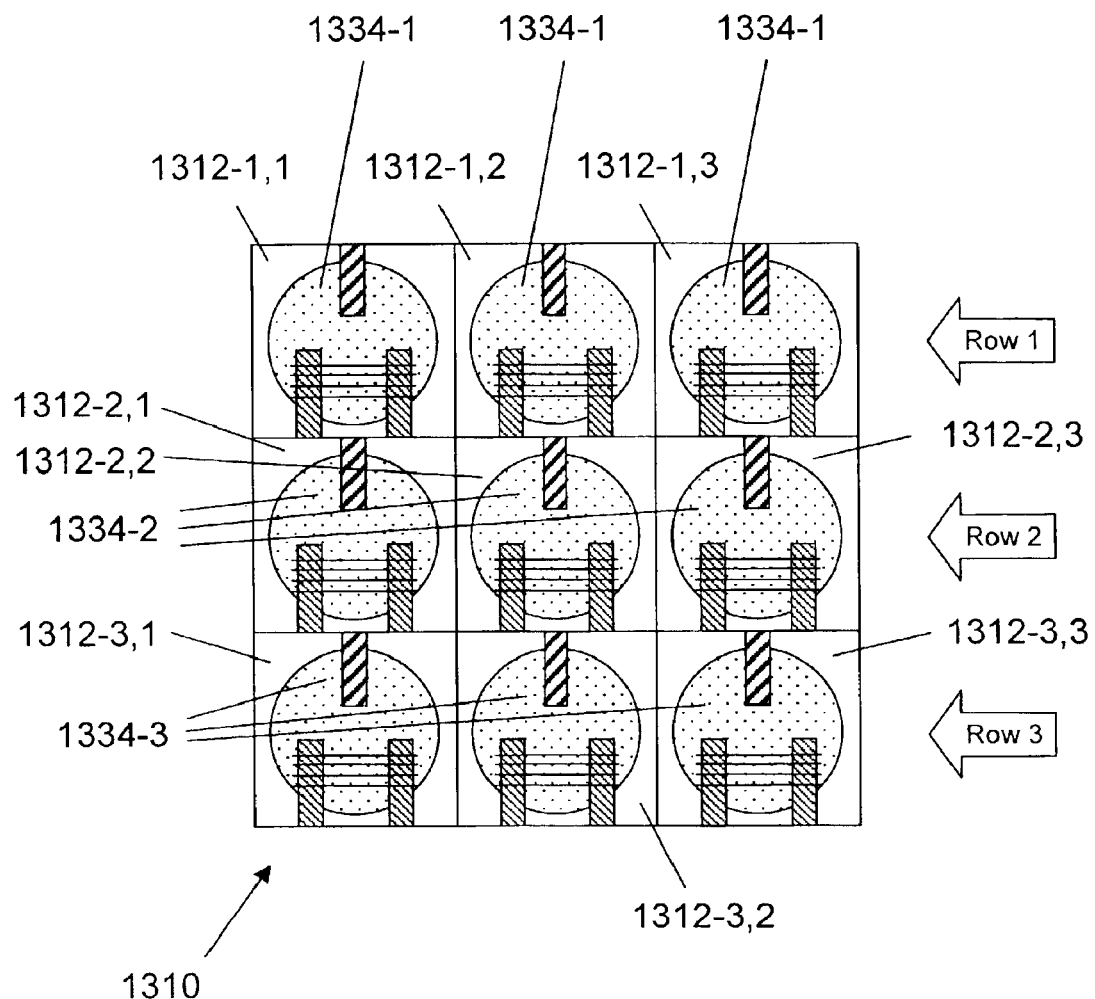
FIG. 13A is a top view of a portion of an array of nanostructure sensing devices onto which reactant drops have been dispensed.

FIG. 13A shows schematically an array 1310 of nanostructure sensing devices 1312-*a,b*. For the purpose of illustration, the array 1310 contains only nine nanostructure sensing devices 1312-1,1–1312-3,3. Of course, in an actual array, there can be as many as $10^6$ or more nanostructure sensing devices, as is known in the art of semiconductor device manufacturing. For the purpose of illustration, three rows 1, 2, 3 of nanostructure sensing devices 1312-*a,b* are shown. Of course, there can be any number of rows of devices. In the illustrated embodiment and as shown in the individual device 1312-*a,b* in FIG. 13B, each nanostructure sensing device 1312-*a,b* includes two contact electrodes 1314-*a,b*-1, 1314-*a,b*-2, a number of nanostructures 1318- a,b, and a counter electrode 1320-a,b, all on a substrate 1316-a,b. In other arrangements, each nanostructure sensing device can include also a pseudo-reference electrode (not shown). The methods disclosed herein are not limited to modification of selectivity for sensing within rows of nanostructure sensing devices, but can apply to any portions of the array for which different selectivity for sensing is desired.

Again with reference to FIG. 13A, in Row 1, drops of reactant 1334-1 have been dispensed from a chemical jet onto each nanostructure sensing device 1312-1,b. In Row 2, drops of reactant 1334-2 have been dispensed from a chemical jet onto each nanostructure sensing device 1312-2,b. In Row 3, drops of reactant 1334-3 have been dispensed from a chemical jet onto each nanostructure sensing device 1312-3,b. In this example, reactants 1334-1, 1334-2, 1334-3 are all electrochemical solutions and each is different from the others. Electrochemical solutions are well known in the art. Possible solutions for modifying selectivity for sensing of nanostructures include those used for electroplating metals, for electro-induced polymerization and for electro-crystallization.

A first voltage is applied to contact electrodes 1314-1,b-1, 1314-1,b-2, and a second voltage, different from the first voltage, is applied to counter electrodes 1320-1,b, thus effecting an electrochemical reaction within the drops of reactant 1334-1. Similarly for the nanostructure sensing devices in Row 2, a third voltage is applied to the contact electrodes 1314-2,b-1, 1314-2,b-2, and a fourth voltage, different from the third voltage is applied to counter electrodes 1320-2,b, thus effecting an electrochemical reaction within the drops of reactant 1334-2. Again for the nanostructure sensing devices in Row 3, a fifth voltage is applied to the contact electrodes 1314-3,b-1, 1314-3,b-2, and a sixth voltage, different from the fifth voltage is applied to counter electrodes 1320-3,b, thus effecting an electrochemical reaction within the drops of reactant 1334-3. The first, third and fifth voltages may or may not be the same. The second, fourth, and sixth voltages may or may not be the same. The electrochemical reactions cause modification of the selectivity for sensing of the nanostructures 1318-a,b within the array 1310.

A pseudo-reference electrode for helping to control the electrochemical reaction, as is known in the art, can be provided. The pseudo-reference electrode can be a component of the chemical jets, and voltages can be applied to effect electro-chemical reactions while the chemical jets are in contact with the drops of reactant. Alternatively, pseudo-reference electrodes can be provided as components of the nanostructure sensing devices, as has been illustrated in FIG. 3. The electrochemical reactions can be monitored and controlled by controlling the potential on the electrodes, the amount of current in the reactions, the concentration of the solution, or by time, as is known in the art. In an alternative arrangement, the nanostructure sensing devices do not include counter electrodes 1320-a,b, but counter electrodes (not shown) are provided in the chemical jets, and the electrochemical reactions occur while the chemical jets are dispensing the drops 1334-1, 1334-2, 1334-3 of reactant.

Figure 13B:
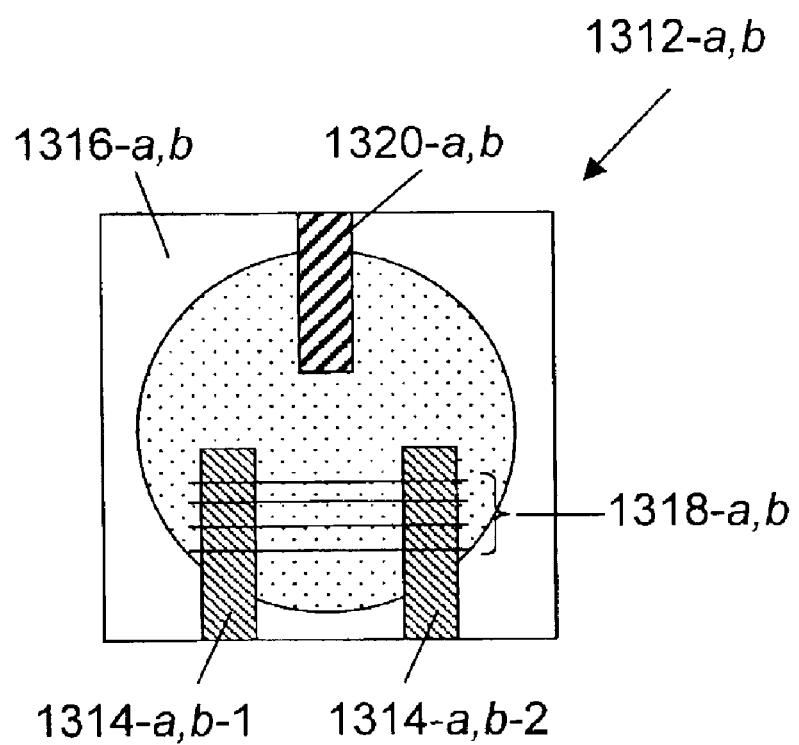
FIG. 13B shows components in an individual nanostructure sensing device from the array of FIG. 13A.

Another embodiment of the invention can be understood with reference to FIGS. 13A, 13B. The array 1310 of nanostructure sensing devices would be as shown in FIG. 13A except that there are no counter electrodes 1320-a,b. The drops 1334-1, 1334-2, 1334-3 of reactant react with the nanostructures 1318-1,b, 1318-2,b, 1318-3,b, respectively, chemically, instead of electrochemically, to modify the selectivity for sensing of the nanostructures 1318-a,b.

Yet another embodiment of the invention can be understood with reference to FIGS. 13A, 13B. Again, the array 1310 of nanostructure sensing devices 1312-a,b is as shown in FIG. 13A except that there are no counter electrodes 1320-a,b. The drops 1334-1, 1334-2, 1334-3 of reactant are dispensed onto the nanostructure sensing devices 1312-1,b, 1312-2,b, 1312-3,b,. FIG. 13A illustrates an arrangement where each drop 1334-1, 1334-2, 1334-3 of reactant is confined to only one nanostructure sensing device. In other arrangements, a drop of reactant 1334-a can extend over many nanostructure sensing devices. A voltage is applied across each pair of contact electrodes 1314-a,b-1, 1314-a,b-2 and a current flows through the connecting nanostructures 1318-a,b. The voltage is increased gradually in each nanostructure sensing device 1312-a,b, thereby gradually increasing current flow through the nanostructures 1318-a,b. The increasing energy from the increasing current flow can lead to a reaction between the nanostructures and the reactant, which causes formation of one or more point defects. When a point defect forms, there is a large increase in resistance, there is a sharp decrease in current flow through the nanostructures, and the reaction stops. The characteristic voltage at which the reaction becomes self-limiting, i.e., at which the reaction stops, can be different for each device. Point defects produced in the self-limiting reaction can have selectivity for sensing chemical species. Point defects can also serve as attachment sites for molecules in further reactions as will be discussed below. In subsequent processing to modify selectivity for sensing of nanostructure sensing devices, it is not necessary to apply an increasing voltage to form the point defects. The previously-found characteristic voltages can be applied for known periods of time until the point defects form and the reaction stops.

In any of the embodiments discussed above with reference to FIGS. 13A, 13B, the modification reaction can be initiated or controlled by supplying to the array additional forms of energy (not shown), such as ultraviolet radiation, thermal energy, or electrical energy.

The chemical jet processes described above can be performed in a controlled atmosphere to mitigate evaporation of the reactant droplets, as is known in the art.

Figure 14A:
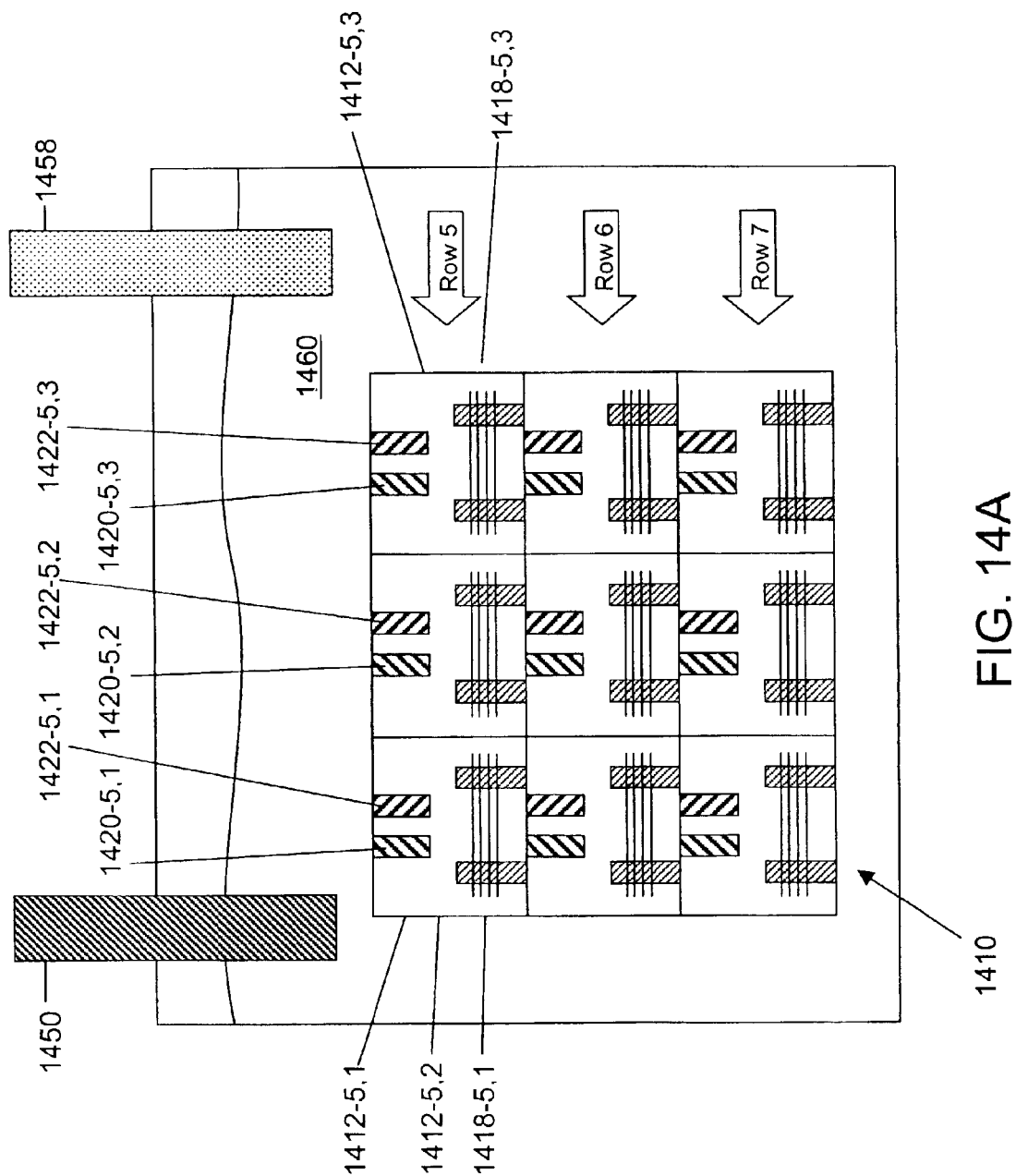
FIG. 14A is a view of a portion of an array of nanostructure sensing devices submerged in a first reactant.
Figure 14B:
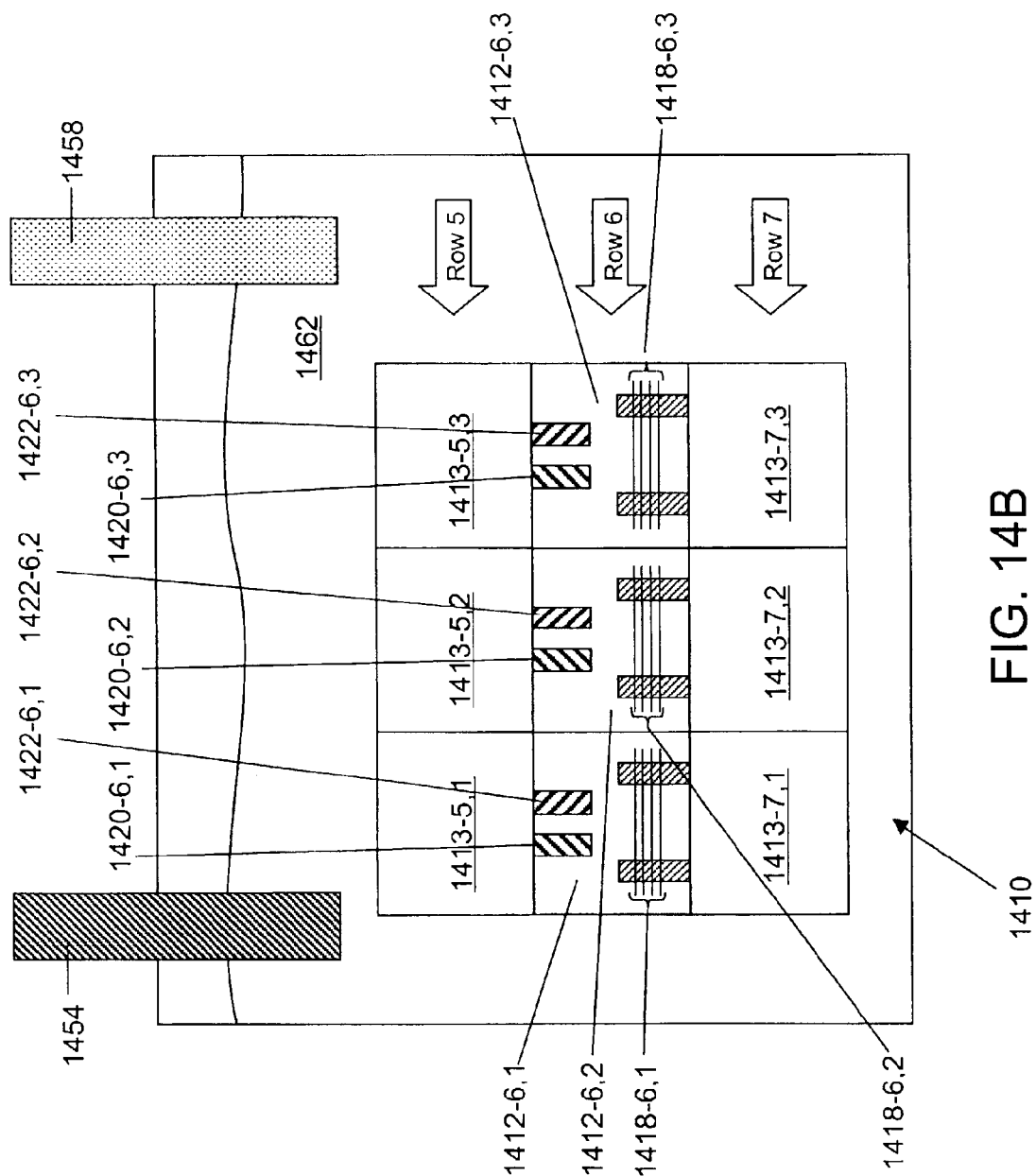
FIG. 14B is a view of a portion of an array of nanostructure sensing devices submerged in a second reactant.
Figure 14C:
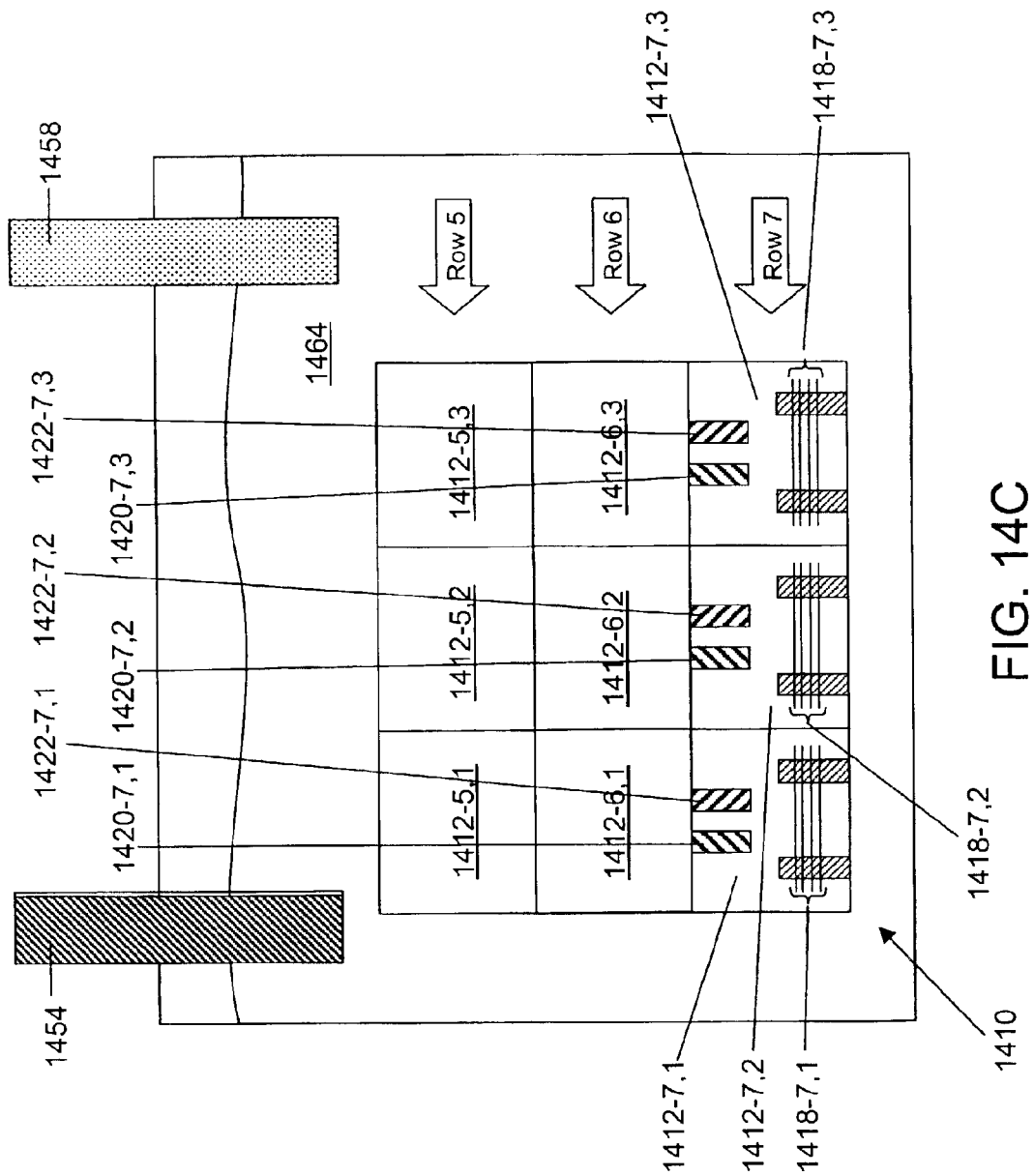
FIG. 14C is a view of a portion of an array of nanostructure sensing devices submerged in a third reactant.

FIG. 14A, 14B, 14C are schematic drawings illustrating a method of making a system for selectively detecting and identifying a predetermined number of chemical species according to another embodiment of the invention. For the purpose of illustration, an array 1410 containing only nine nanostructure sensing devices 1412-a,b is shown. Of course, in an actual array, there can be any number of nanostructure sensing devices, as in known in the art of semiconductor manufacturing. In the illustrated embodiment, each nanostructure sensing device 1412-a,b includes two contact electrodes 1414-a,b-1, 1414-a,b-2 a number of nanostructures 1418-a,b, and may also include a counter electrode 1420-a,b and a pseudo-reference electrode 1422-a,b, wherein a is an integer indicating the row number and b is an integer indicating the column number in the array where the feature is located. Each nanostructure sensing device 1412-a,b is electrically insulated from the other nanostructure sensing devices. For the purpose of illustration, three rows 5, 6, 7 of nanostructure sensing devices are indicated. Of course, there can be any number of rows of devices. Furthermore, the methods disclosed herein are not limited to modification of selectivity for sensing within rows of nanostructure sensing devices, but can apply to any portions of the array for which different selectivity for sensing is desired.

In FIG. 14A, the entire array 1410 has been submerged in a first reactant bath 1460. Alternatively, only a portion of the array 1410, for which modification of selectivity for sensing is desired, such as Row 5, can be submerged in the reactant bath 1460. In the example illustrated in FIGS. 14A–14C, each nanostructure sensing device includes two contact electrodes 1414-a,b-1, 1414-a,b-2 a number of nanostructures 1418-a,b, and a counter electrode 1420-a,b, wherein a is an integer indicating the row number and b is an integer indicating the column number in the array where the feature is located. In other arrangements, each nanostructure sensing device 1412-a,b can include also a pseudo-reference electrode 1422-a,b. For the purpose of illustration, three rows 5, 6, 7 of nanostructure sensing devices are shown. Of course, there can be any number of rows of devices. The methods disclosed herein are not limited to modification of selectivity for sensing within rows of nanostructure sensing devices, but can apply to any portions of the array for which different selectivity for sensing is desired. In this example, reactant 1460 contains an electrochemical solution. A first voltage is applied to contact electrodes 1414-5,b-1, 1414-5,b-2 and a second voltage, different from the first voltage is applied to counter electrodes 1420-5, b, thus effecting an electrochemical reaction between the electrochemical solution 1460 and the nanostructures 1418-5,b and causing modification of the selectivity for sensing of the nanostructures 1418-5,b within the array 1410. After modification of nanostructures 1418-5,b, the array 1410 is removed from the reactant bath 1460, and the array 1410 is rinsed.

In FIG. 14B, the entire array 1410 has been submerged in a second reactant bath 1462. The details of structures on only Row 6 are shown. Alternatively, only a portion of the array 1410, for which modification of selectivity for sensing is desired, such as Row 6, can be submerged in the reactant bath 1462. In this example, reactant 1462 contains an electrochemical solution. A first voltage is applied to contact electrodes 1414-6,b-1, 1414-6,b-2 and a second voltage, different from the first voltage is applied to counter electrodes 1420-6,b, thus effecting an electrochemical reaction between the electrochemical solution 1462 and the nanostructures 1418-6,b and causing modification of the selectivity for sensing of the nanostructures 1418-6,b within the array 1410. After modification of nanostructures 1418-6,b, the array 1410 is removed from the reactant bath 1462, and the array 1410 is rinsed.

In FIG. 14C, the entire array 1410 has been submerged in a third reactant bath 1464. The details of structures on only Row 7 are shown. Alternatively, only a portion of the array 1410, for which modification of selectivity for sensing is desired, such as Row 7, can be submerged in the reactant bath 1464. In this example, reactant 1464 contains an electrochemical solution. A first voltage is applied to contact electrodes 1414-7,b-1, 1414-7,b-2 and a second voltage, different from the first voltage is applied to counter electrodes 1420-7,b, thus effecting an electrochemical reaction between the electrochemical solution 1464 and the nanostructures 1418-7,b and causing modification of the selectivity for sensing of the nanostructures 1418-7,b within the array 1410. After modification of nanostructures 1418-7,b, the array 1410 is removed from the reactant bath 1464, and the array 1410 is rinsed.

The electrochemical reactions can be monitored and controlled by controlling the potential on the electrodes, the amount of current in the reactions, the concentration of the solution, or by time, as is known in the art.

FIGS. 14A, 14B, 14C show nanostructure sensing devices 1412-a,b that each include a counter electrode 1420-a,b. In an alternative arrangement, the nanostructure sensing devices 1412-a,b do not include counter electrodes 1420-a, b, and a counter electrode 1450, 1452, 1454 is provided in each reactant bath 1460, 1462, 1464, respectively. The counter electrodes 1450, 1452, 1454 in each reactant bath 1460, 1462, 1464, respectively can be the same or they can be different.

A pseudo-reference electrode can be used to help control the electrochemical reaction, as is known in the art. A pseudo-reference electrode 1458 can be provided in contact with the reactant baths 1460, 1462, 1464. Alternatively, pseudo-reference electrodes 1422-a,b can be provided within the nanostructure sensing devices 1412-a,b, as has been illustrated above in FIGS. 14A, 14B, 14C.

A method of fabricating an electronic system for selectively detecting and identifying a predetermined number of chemical species according to another embodiment of the invention can be understood with reference to FIGS. 14A, 14B, 14C. Again, the array 1410 of nanostructure sensing devices 1412-a,b is as shown in FIGS. 14A, 14B, 14C except that there are no counter electrodes 1420-a,b, nor pseudo-reference electrodes 1422-a,b. The array 1410 is submerged or partially submerged in the reactant bath 1460. A voltage is applied across each pair of contact electrodes 1414-5,b-1, and a current flows through the nanostructures 1418-5,b. The voltage is increased gradually in each nanostructure sensing device 1412-5,b, thereby gradually increasing current flow through the nanostructures. The increasing energy from the increasing current flow can lead to a reaction between the nanostructures and the reactant, causing formation of one or more point defects. When the point defect forms, there is a large increase in resistance, a sharp decrease in current flow through the nanostructures, and the reaction stops. The characteristic voltage at which the reaction becomes self-limiting, i.e., at which the reaction stops, can be different for each device. In subsequent processing to modify selectivity for sensing of nanostructure sensing devices, it is not necessary to apply an increasing voltage to form the point defects. The previously-found characteristic voltages can be applied for known periods of time until the point defects form and the reaction stops. After modification of nanostructures 1418-5,b, the array 1410 is removed from the reactant bath 1460, and the array 1410 is rinsed.

The array 1410 is submerged or partially submerged in the reactant bath 1462. A voltage is applied across each pair of contact electrodes 1414-6,b-1, 1414-6,b-2 and a current flows through the nanostructures 1418-6,b. The voltage is increased gradually in each nanostructure sensing device 1412-6,b, thereby gradually increasing current flow through the nanostructures. The increasing energy from the increasing current flow can lead to a reaction between the nanostructures 1418-6,b and the reactant 1462, causing formation of one or more point defects. When the point defect forms, there is a large increase in resistance, a sharp decrease in current flow through the nanostructures, and the reaction stops. The characteristic voltage at which the reaction becomes self-limiting, i.e., at which the reaction stops, can be different for each device. In subsequent processing to modify selectivity for sensing of nanostructure sensing devices, it is not necessary to apply an increasing voltage to form the point defects. The previously-found characteristic voltages can be applied for known periods of time until the point defects form and the reaction stops. After modification of nanostructures 1418-6,b, the array 1410 is removed from the reactant bath 1462, and the array 1410 is rinsed.

The array 1410 is submerged or partially submerged in the reactant bath 1464. A voltage is applied across each pair of contact electrodes 1414-7,b-1, 1414-7,b-2 and a current flows through the nanostructures 1418-7,b. The voltage is increased gradually in each nanostructure sensing device 1412-7,b, thereby gradually increasing current flow through the nanostructures 1418-7,b. The increasing energy from the increasing current flow can lead to a reaction between the nanostructures 1418-7,b and the reactant 1464, causing formation of one or more point defects. When the point defect forms, there is a large increase in resistance, a sharp decrease in current flow through the nanostructures, and the reaction stops. The characteristic voltage at which the reaction becomes self-limiting, i.e., at which the reaction stops, can be different for each device. In subsequent processing to modify selectivity for sensing of nanostructure sensing devices, it is not necessary to apply an increasing voltage to form the point defects. The previously-found characteristic voltages can be applied for known periods of time until the point defects form and the reaction stops. After modification of nanostructures 1418-7,b, the array 1410 is removed from the reactant bath 1464, and the array 1410 is rinsed.

In any of the embodiments discussed above with reference to FIGS. 14A, 14B, 14C, the modification reaction can be initiated or controlled by supplying to the array additional forms of energy (not shown), such as ultraviolet radiation, thermal energy, or electrical energy.

Figure 15:
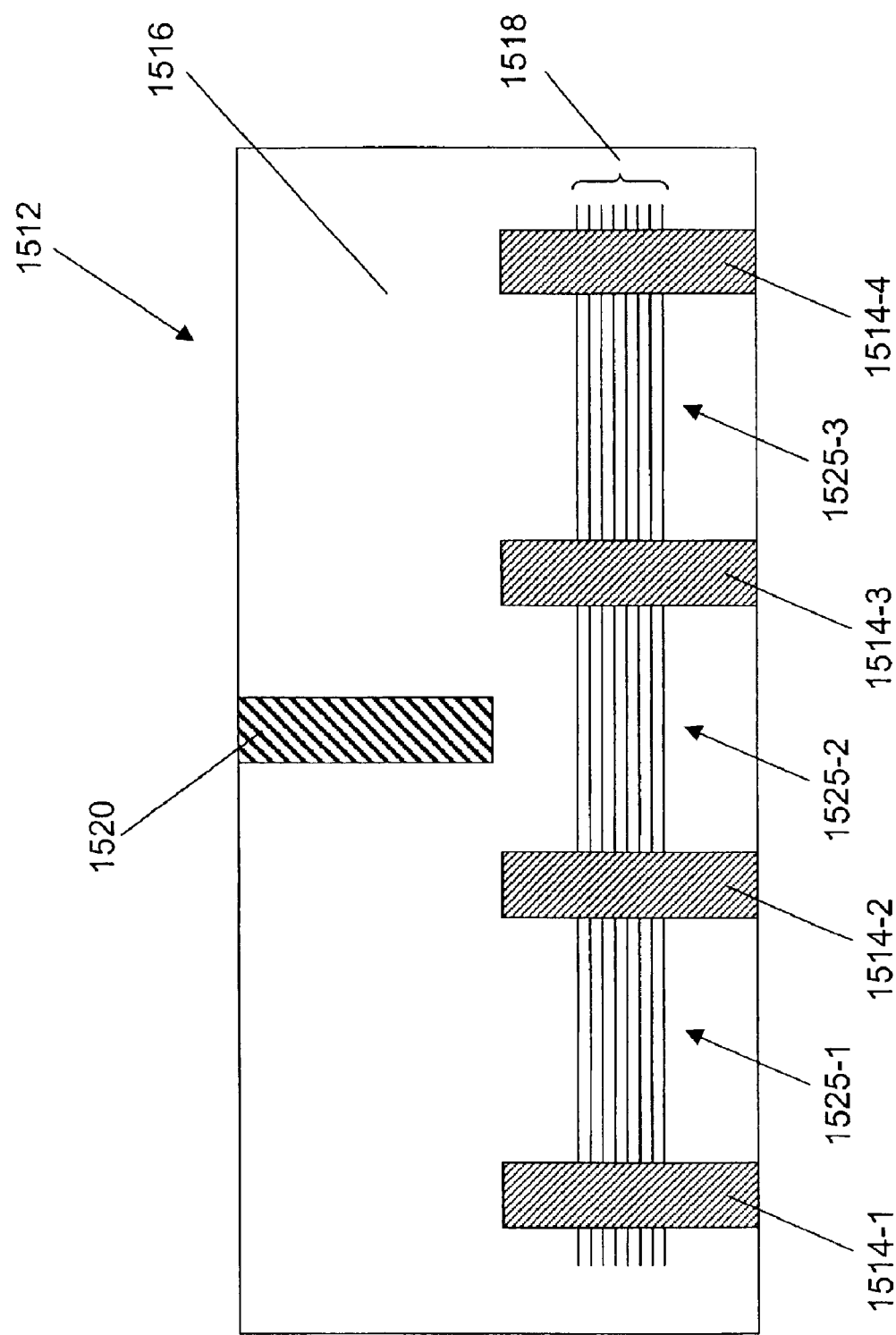
FIG. 15 shows an example of a nanostructure sensing device that has nanostructures extending across four electrodes.

Although many of the illustrated embodiments show nanostructure sensing devices with only two contact electrodes, any number of contact electrodes can be used. FIG. 15 illustrates a nanostructure sensing device 1512 in another arrangement that contains four contact electrodes 1514-1, 1514-2, 1514-3, 1514-4 on a substrate 1516. Nanostructures 1518 span across and are in electrical contact with at least some of the contact electrodes 1514-1, 1514-2, 1514-3, 1514-4. Nanostructure section 1525-1 spans the region between contact electrode 1514-1 and 1514-2. Nanostructure section 1525-2 spans the region between contact electrode 1514-2 and 1514-3. Nanostructure section 1525-3 spans the region between contact electrode 1514-3 and 1514-4.

The nanostructures 1518 of FIG. 15 can be modified for selectivity for sensing by any of the methods discussed above for FIG. 13 and FIGS. 14A, 14B, 14C. The methods include chemical, electrochemical and self-limiting reactions. Reactants can be provided through chemical jets or in a reactant bath. A counter electrode 1520 and a pseudo-reference electrode (not shown) for electrochemical reactions can be supplied in the nanostructure sensing device 1512, in the reactant bath or in the chemical jet.

When chemical methods are used for modification of selectivity for sensing, all sections 1525-1, 1525-2, 1525-3 are modified in the same way, unless one or more sections is shielded from the reactant. Alternatively, for electrochemical methods and self-limiting reactions, each section 1525-1, 1525-2, 1525-3 can be modified separately by applying voltages only to electrodes 1514-1 and 1514-3, 1514-2 and 1514-3, and 1514-3 and 1514-4, respectively. For example, when a first voltage is applied to contact electrodes 1514-1 and 1514-2, and a second voltage, different from the first voltage is applied to counter electrode 1520, in the presence of an electrochemical solution, selectivity for sensing for only nanostructure section 1525-1 is modified. If the first voltage is applied to contact electrodes 1514-1 and 1514-3, selectivity for sensing for both nanostructure sections 1525-1, 1525-2 is modified. As described above, any section 1525-1, 1525-2, 1525-3 can be shielded from the electrochemical solution to prevent modification.

In another example, the device 1512 in FIG. 15 is immersed in a liquid or gas reactant. A first voltage is applied to contact electrode 1514-2 and a second voltage, different from the first voltage, is applied to contact electrode 1514-3, and current flows through nanostructure section 1525-2. As both the first and second voltages are increased gradually, current flow through the nanostructure section 1525-2 increases. The increasing energy from the increasing current flow can lead to a reaction between the nanostructure section 1525-2 and the reactant, causing formation of one or more point defects, as discussed above. When the point defect forms, there is a large increase in resistance, a sharp decrease in current flow through the nanostructure section 1525-2, and the reaction stops.

Figure 16A:
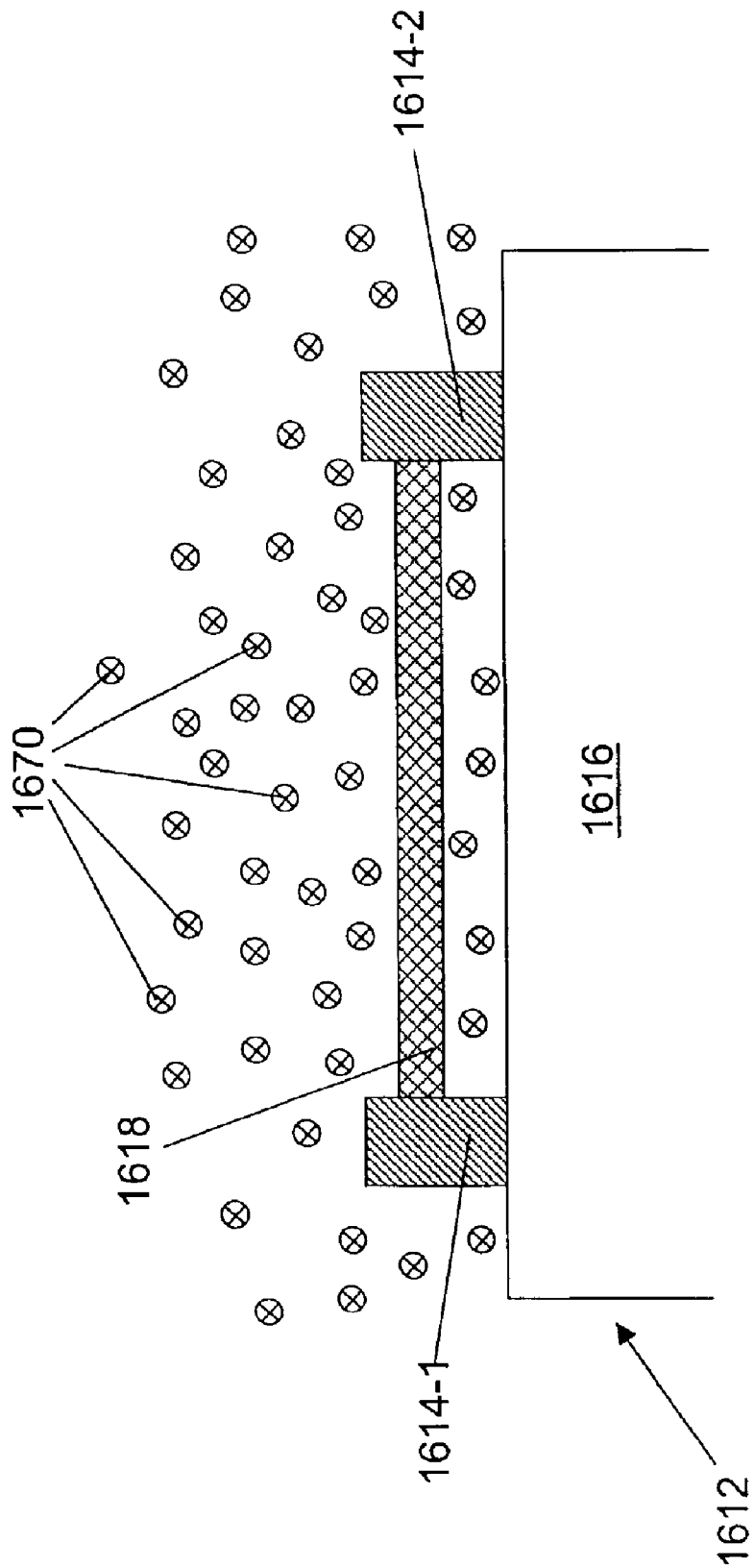
FIG. 16A is a side view of a nanostructure sensing device attached to two contact electrodes and surrounded by a reactant.
Figure 16B:
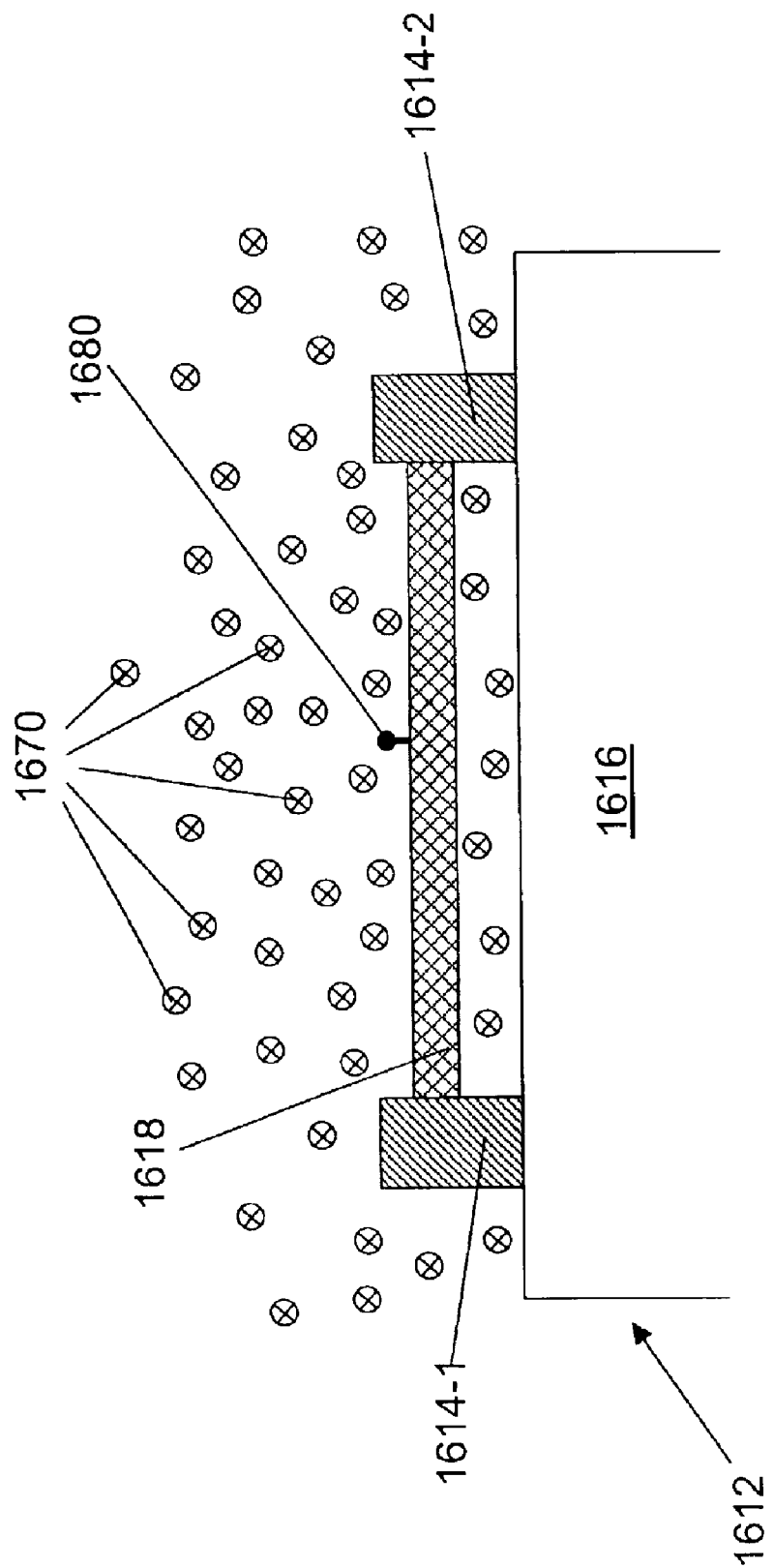
FIG. 16B is a side view of the nanostructure sensing device of FIG. 16A after a voltage has been applied across the two electrodes and a point defect has formed on the nanostructure.
Figure 16C:
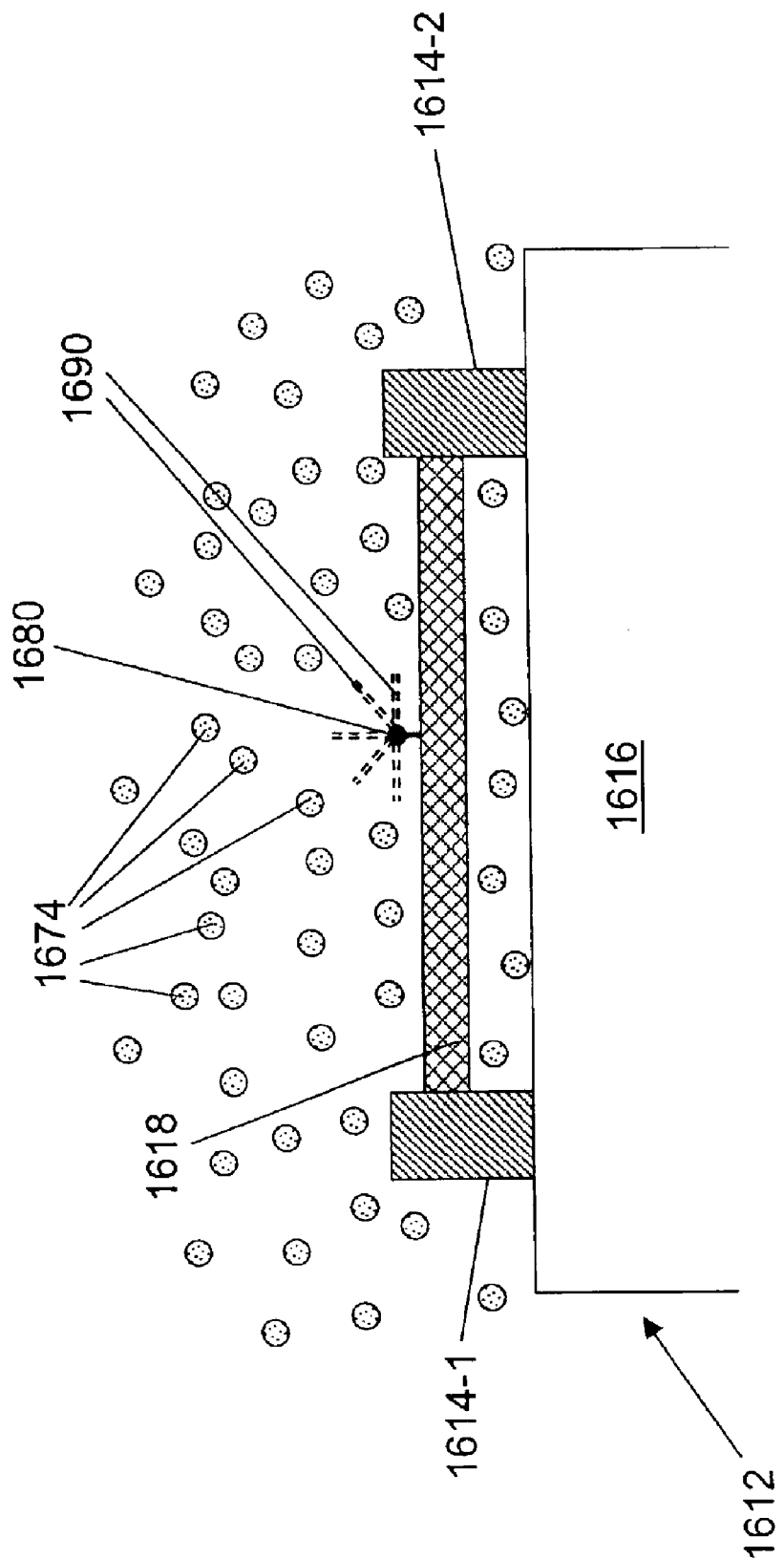
FIG. 16C is a side view of the nanostructure sensing device of FIG. 16B after a second reactant has been introduced, and a variety of molecules have attached to form a structure extending from the point defect.

FIGS. 16A, 16B, 16C show a method of modifying selectivity for sensing for a nanostructure in a nanostructure sensing device according to an illustrated embodiment of the invention.

FIG. 16A shows a side view of an individual nanostructure sensing device 1612 that includes two contact electrodes 1614-1, 1614-2 on a substrate 1616. A nanostructure 1618 is suspended above the substrate 1616 and is in contact with the two contact electrodes 1614-1, 1614-2, forming a conductive link therebetween. Although only one nanostructure 1618 is shown in the illustration of FIG. 16A, any number of nanostructures 1618 can make contact with the two contact electrodes 1614-1, 1614-2. The nanostructure 1618 is surrounded by reactant molecules 1670. The reactant molecules 1670 can be in the form of a liquid or a gas. The reactant molecules 1670 can be supplied by any of the methods described above or by any other method that will expose the nanostructure 1618 to the reactant molecules 1670.

In FIG. 16B, a voltage is applied across the contact electrodes 1614-1, 1614-2, causing a current to flow through the nanostructure 1618. The voltage is increased gradually, thus gradually increasing the current flow through the nanostructure 1618. The increasing energy from the increasing current flow can lead to a reaction between the nanostructure 1618 and the reactant molecules 1670, causing formation of one or more point defects. At a characteristic voltage a point defect 1680 forms, there is a large increase in resistance, a sharp decrease in current flow through the nanostructure 1618, and the reaction stops. Thus, a point defect 1680 is formed on the surface of the nanostructure 1618 by a self-limiting reaction. In other arrangements, more than one point defect 1680 can form before the reaction stops. In subsequent processing to modify selectivity for sensing of nanostructure sensing devices, it is not necessary to apply an increasing voltage to form the point defects. The previously-found characteristic voltages can be applied for known periods of time until the point defects form and the reaction stops. In some embodiments, the point defect 1680 has a selectivity for sensing chemical species.

FIG. 16C shows a resulting structure extending from the surface of the nanostructure 1618 after a few additional steps have been performed. The structure shown in FIG. 16B has been rinsed with another gas or liquid, containing second reactant molecules 1674. The second reactant molecules 1674 attach to the point defect 1680. There can be individual attachments of second reactant molecules 1674 or a series of attachments of second reactant molecules 1674, thus forming extended structures 1690 from the point defect 1680. The attached molecules 1674 or the extended structures 1690 can have selectivity for sensing chemical species. In other arrangements, reactant molecules 1670 are rinsed away by a non-reacting gas or liquid (not shown) before the nanostructure is exposed to second reactant molecules 1674.

Although the example illustrated in FIGS. 16A, 16B, 16C includes only two kinds of reactant molecules 1670, 1674, a whole series of different reactants can be used to build sensing structures extending from the point defect. It can be desirable to use a series of different reactants to build a sensing structure, for example, when a molecule that can sense the chemical species of interest cannot attach itself to the nanostructure directly. A different molecule can be attached to the nanostructures, and one or more intermediary molecules can be linked, one to the other, to provide a suitable linking site for a sensing molecule.

Figure 17:
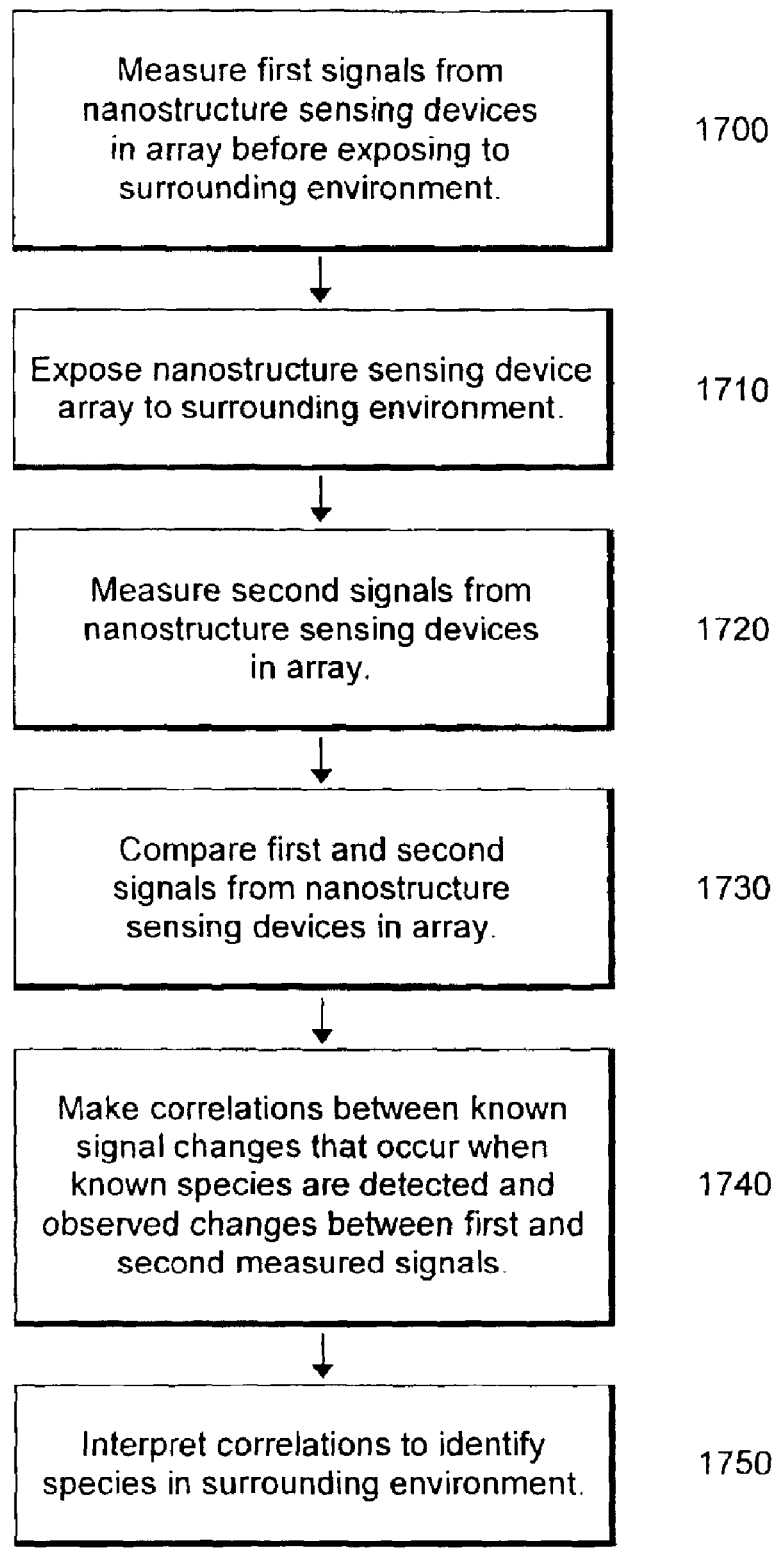
FIG. 17 is a flow chart showing a method for selectively detecting chemical or biological species according to an embodiment of the invention.

FIG. 17 shows a flow chart that summarizes the steps for detecting a plurality of chemical or biological species in a surrounding environment according to an embodiment of the invention. In Step 1700, before exposing a sensor array to a surrounding environment of interest, first signals are measured from the nanostructure sensing devices in the array. In Step 1710, the sensor array is exposed to the surrounding environment. Second signals are measured from the nanostructure sensing devices in the array in Step 1720. In Step 1730, the first signals and the second signals from the nanostructure sensing devices in the array are compared. In Step 1740, correlations are made between known signal changes that occur when known chemical or biological species are detected and observed changes between the first signal and the second signal from the nanostructure sensing devices in the array. Step 1750 involves interpreting the correlations of Step 1740 to identify the species in the surrounding environment. Signals can include electrical responses, optical responses, thermal responses, and mechanical responses.

In another arrangement, a first gate voltage can be applied to gate electrodes associated with nanostructure sensing devices in at least a first portion of the array before Step 1700 and maintained throughout the both the first and second signal measurements. A second gate voltage, different from the first gate voltage, can be applied to gate electrodes associated with nanostructure sensing devices in at least a second portion of the array before Step 1700 and maintained throughout the both the first and second signal measurements. In general, different gate voltages can be used for different portions of the array. Gate voltages can be chosen to optimize the response of the nanostructure sensing devices to the chemical or biological species of interest.

In yet another arrangement, within any portion of the array of nanostructure sensing devices a series of different gate voltages can be applied to the gate electrodes associated with each nanostructure sensing device. A series of first and second signal measurements, as described in FIG. 17, are made at each gate voltage, that is, the first and second signals are measured as a function of gate voltage. The differences between measured first and second signals at each gate voltage can be correlated to known differences between first and second signals at each gate voltage when known chemical or biological species are detected. These correlations are used to identify the species in the surrounding environment.

Figure 18:
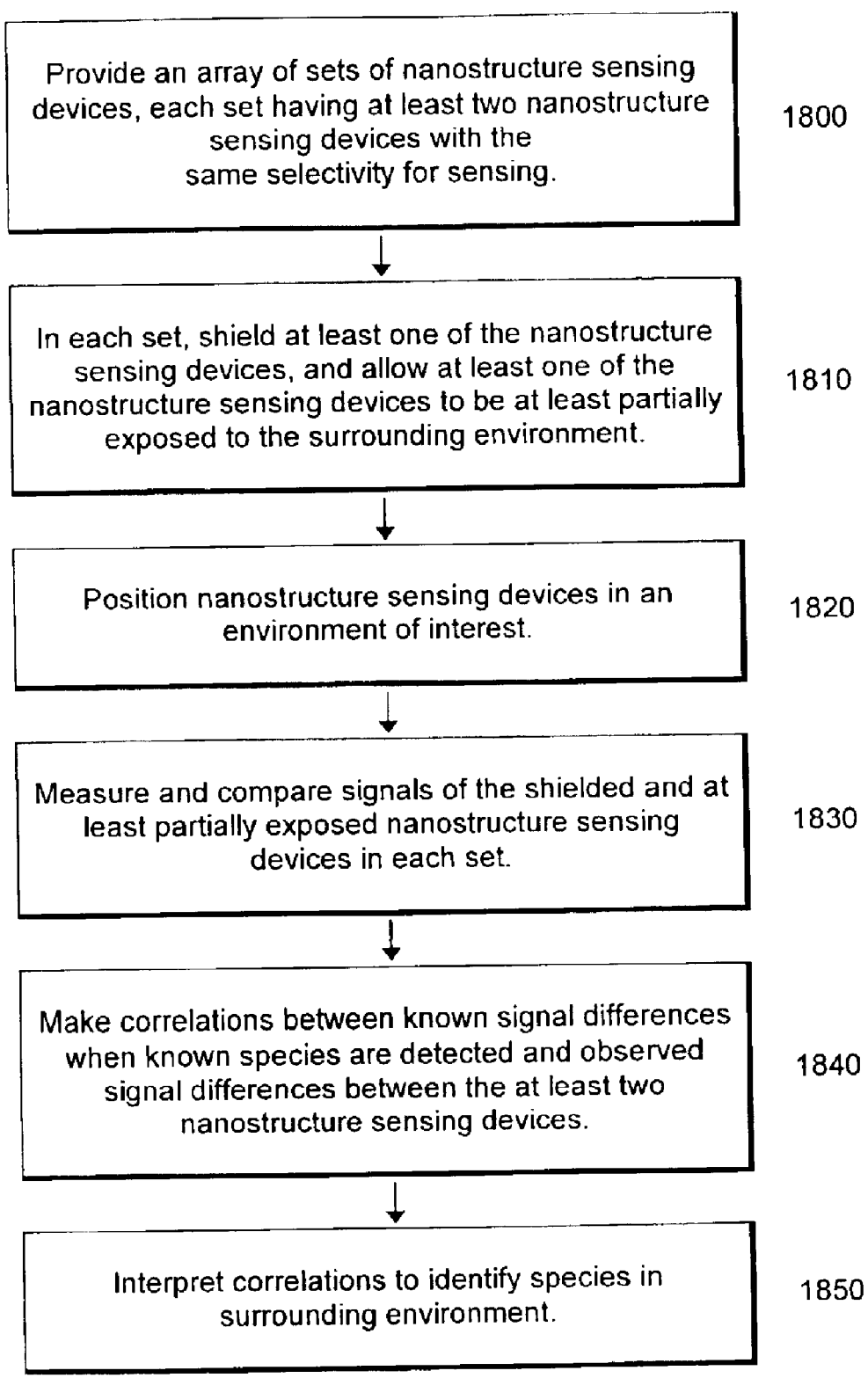
FIG. 18 is a flow chart showing a method for selectively detecting chemical or biological species according to another embodiment of the invention.

FIG. 18 shows a flow chart that summarizes the steps for detecting a plurality of chemical or biological species in a surrounding environment according to another embodiment of the invention. In Step 1800, an array of sets of nanostructure sensing devices is provided. Each set has at least two nanostructure sensing devices with the same selectivity for sensing. In Step 1810, within each set, at least one of the at least two nanostructure sensing devices is shielded from the surrounding environment, and at least one of the at least nanostructure sensing devices is allowed to be at least partially exposed to the surrounding environment. The nature of the shielding and the at least partial exposure of the nanostructure sensing devices has been discussed in detail above with reference to FIG. 6. In Step 1820, the nanostructure sensing devices are positioned in an environment of interest. Signals from both the shielded and at least partially exposed nanostructure sensing devices are measured and compared in Step 1830. In Step 1840, correlations are made between differences between known signal differences when known chemical or biological species are detected and observed signal differences between the shielded devices and the partially-shielded devices. Step 1850 involves interpreting the correlations of Step 1840 to identify the species in the surrounding environment. Signals can include electrical responses, optical responses, thermal responses, and mechanical responses.

In another arrangement, a first gate voltage can be applied to gate electrodes associated with each of the at least two nanostructure sensing devices in each set in at least a first portion of the array of sets before Step 1830 and maintained while measuring and comparing signals from the at least two nanostructure sensing devices in each set. A second gate voltage, different from the first gate voltage, can be applied to gate electrodes associated with each of the at least two nanostructure sensing devices in each set in at least a second portion of the array of sets before Step 1830 and maintained while measuring and comparing the signals from the at least two nanostructure sensing devices in each set. In general, different gate voltages can be used for different portions of the array of sets. Gate voltages can be chosen to optimize the response of the nanostructure sensing devices to the chemical or biological species of interest.

In yet another arrangement, a series of different gate voltages can be applied to gate electrodes associated with each of the at least two nanostructure sensing devices in each set in at least a portion of the array of sets and maintained while measuring and comparing the signals from the at least two nanostructure sensing devices in each set at each gate voltage, that is, the signals are measured and compared as a function of gate voltage. Correlations are made between known signal differences at each gate voltage when known chemical or biological species are detected and the measured signal differences at each gate voltage between the at least two nanostructure sensing devices in each set. These correlations are used to identify the species in the surrounding environment.

The correlations between measured signals and known signals as described above for FIGS. 17 and 18 can be made through algorithms, such as primary component analysis, which have been developed and used for similar sensing arrays using different sensor technologies. An example of such an algorithm is discussed by Shaffer in U.S. Pat. No. 6.289,328, which is incorporated in its entirety herein by reference.

Areas of application include industrial, medical, agricultural, and environmental monitoring. These can include characterization of water and air for pollutants and biotoxins, both gaseous and liquid chemicals in processing or manufacturing, body fluids (urine, blood, etc.), and breath. For medical applications, the sensors can be used externally on samples or placed in situ for continuous monitoring. As the demand for sensing in military applications, such as for detection of harmful chemical and biological agents, continues to increase, nanostructure sensing device arrays, as described herein are ideally suited to fill this demand. Other applications include sensing simple odors, such as for foodstuffs, drinks, perfumes and essential oils.

This invention has been described herein in considerable detail to provide those skilled in the art with information relevant to apply the novel principles and to construct and use such specialized components as are required. However, it is to be understood that the invention can be carried out by different equipment, materials and systems, and that various modifications, both as to the equipment and operating procedures, can be accomplished without departing from the scope of the invention itself.

We claim:

1. An electronic system for selectively detecting and identifying a plurality of chemical or biological species, comprising:
   an array of nanostructure sensing devices containing:
      a first nanostructure sensing device comprising a first nanostructure, at least two contact electrodes electrically connected by the first nanostructure and a protective coating on the contact electrodes, the first nanostructure sensing device having a selectivity for sensing a first species;
      a second nanostructure sensing device comprising a second nanostructure, at least two contact electrodes electrically connected by the second nanostructure and a protective coating on the contact electrodes, the second nanostructure sensing device having a selectivity for sensing a second species; and
      a processing system to deconvolute and analyze signals from the array to provide identification of chemical or biological species.

2. The electronic system of claim 1, wherein the contact electrodes comprise a material selected from the group consisting of aluminum, copper, titanium and tungsten.

3. The electronic system of claim 1, wherein the protective coating is selected from the group consisting of silicon oxides, metal oxides, polymer films, and nonvolatile organics.

4. The electronic system of claim 1, further comprising a gate electrode in the first nanostructure sensing device.

5. The electronic system of claim 1, further comprising a counter electrode, electrically isolated from the contact electrodes, in the first nanostructure sensing device.

6. The electronic system of claim 5, further comprising a pseudo-reference electrode, electrically isolated from the contact electrodes, in the first nanostructure sensing device.

7. The electronic system of claim 1, wherein the first nanostructure and the second nanostructure are selected from the group consisting of single-walled nanotubes, multi-walled nanotubes, nanofibers, nanowires, nanocoils, nanospheres, nanocages, nanococoons, nanohorns, nanoropes, nanotori, nanorods, nanoplatelets, and other extended molecules such as polymers, dendrimers, organometallics, fullerene-like molecules, and combinations thereof.

8. The electronic system of claim 1, wherein the first nanostructure and the second nanostructure have approximately linear forms.

9. The electronic system of claim 1, wherein the first nanostructure and the second nanostructure comprise elements selected from the group consisting of boron, carbon, combinations thereof, and combinations with nitrogen.

10. The electronic system of claim 1, further comprising third and fourth nanostructure sensing devices having the same selectivity for sensing as the first nanostructure sensing device, wherein the first nanostructure sensing device is at least partially exposed to the plurality of species and to water, the third nanostructure sensing device is shielded from the plurality of species but not from water, and the fourth nanostructure sensing device is shielded from the plurality of species and from water.

11. The electronic system of claim 10, wherein the third nanostructure sensing device is shielded by a molecular sieve membrane.

12. The electronic system of claim 11, wherein the molecular sieve membrane contains an alumino silicate zeolite.

13. The electronic system of claim 1, further comprising third and fourth nanostructure sensing devices having the same selectivity for sensing as the first nanostructure sensing device, wherein the first nanostructure sensing device is at least partially exposed to the plurality of species and to water, the third nanostructure sensing device is at least partially exposed to the plurality of species but not to water, and the fourth nanostructure sensing device is shielded from the plurality of species and from water.

14. The electronic system of claim 13, wherein the third nanostructure sensing device contains a hydrophobic membrane.

15. The electronic system of claim 14, wherein the hydrophobic membrane contains a siliceous zeolite.

16. The electronic system of claim 14, wherein the hydrophobic membrane contains a fluoropolymer.

17. An electronic system for selectively detecting and identifying a plurality of chemical or biological species, comprising:
   (a) an array of nanostructure sensing devices including:
      a first nanostructure sensing device having a selectivity for sensing a first species, and comprising a first nanostructure and at least two contact electrodes, the contact electrodes electrically connected by the first nanostructure;
      a second nanostructure sensing device having a selectivity for sensing a second species, and comprising a second nanostructure and at least two contact electrodes, the contact electrodes electrically connected by the second nanostructure;
      at least one of the first and second nanostructure sensing devices further including a gate electrode; and
   (b) a processing system to deconvolute and analyze signals from the array to provide identification of chemical or biological species.

18. The electronic system of claim 17, further comprising a protective coating on the contact electrodes.

19. The electronic system of claim 18 wherein the protective coating is selected from the group consisting of silicon oxides, metal oxides, polymer films, and nonvolatile organics.

20. The electronic system of claim 17, further comprising a counter electrode, electrically isolated from the contact electrodes, in the first nanostructure sensing device.

21. The electronic system of claim 20, further comprising a pseudo-reference electrode, electrically isolated from the contact electrodes, in the first nanostructure sensing device.

22. The electronic system of claim 17, wherein the first nanostructure and the second nanostructure are selected from the group consisting of single-walled nanotubes, multi-walled nanotubes, nanofibers, nanowires, nanocoils, nanospheres, nanocages, nanococoons, nanohorns, nanoropes, nanotori, nanorods, nanoplatelets, and other extended molecules such as polymers, dendrimers, organometallics, fullerene-like molecules, and combinations thereof.

23. The electronic system of claim 17, wherein the first nanostructure and the second nanostructure have approximately linear forms.

24. The electronic system of claim 17, wherein the first nanostructure and the second nanostructure comprise elements selected from the group consisting of boron, carbon, combinations thereof, and combinations with nitrogen.

* * * * *